United States Patent
Basu et al.

(10) Patent No.: US 10,565,663 B1
(45) Date of Patent: Feb. 18, 2020

(54) SYSTEMS AND METHODS FOR ANALYZING RESOURCE PRODUCTION

(71) Applicant: DataInfoCom USA, Inc., Austin, TX (US)

(72) Inventors: Atanu Basu, Austin, TX (US); Daniel Mohan, Austin, TX (US); Chun Wang, Austin, TX (US); Frederick Venter, Driftwood, TX (US)

(73) Assignee: DataInfoCom USA, Inc., Austin, TX (US)

( * ) Notice: Subject to any disclaimer, the term of this patent is extended or adjusted under 35 U.S.C. 154(b) by 468 days.

(21) Appl. No.: 15/052,621

(22) Filed: Feb. 24, 2016

Related U.S. Application Data

(60) Provisional application No. 62/246,121, filed on Oct. 25, 2015, provisional application No. 62/195,775, (Continued)

(51) Int. Cl.
*G06Q 50/02* (2012.01)
*G01V 99/00* (2009.01)
(Continued)

(52) U.S. Cl.
CPC ......... *G06Q 50/02* (2013.01); *E21B 41/0092* (2013.01); *E21B 43/11* (2013.01);
(Continued)

(58) Field of Classification Search
CPC .. G06Q 50/02; G06Q 10/06375; G06N 3/126; G06N 99/005; G01V 99/005;
(Continued)

(56) References Cited

U.S. PATENT DOCUMENTS

| 4,449,896 A | 5/1984 | Klepper et al. |
| 6,021,377 A | 2/2000 | Dubinsky |

(Continued)

FOREIGN PATENT DOCUMENTS

RU 2219337 12/2003

OTHER PUBLICATIONS

Al-Yami et al. "Expert System for the Optimal Design and Execution of Successful Completion Practices Using Artificial Bayesian Intelligence" SPE 143826 (2011): Society of Petroleum Engineers [retrieved on May 3, 2018]. Retrieved from <https://www.onepetro.org/conference-paper/SPE-143826-MS>.*

(Continued)

*Primary Examiner* — Rehana Perveen
*Assistant Examiner* — Alfred B Wechselberger
(74) *Attorney, Agent, or Firm* — Chad Peterson

(57) ABSTRACT

A method for completing a well includes receiving completion parameters associated with wells within a field. The completion parameters including casing parameters, perforation parameters, and fracking parameters. The method further includes determining a field-specific model utilizing the completion parameters and prescribing a completion recipe using a completion analysis engine applied to the field-specific model. The completion recipe includes prescribed perforation parameters and prescribed fracking parameters. The completion analysis engine includes a neural network derived from the field-specific model or regression of a correlation of features in the field-specific model. The method also includes completing the well in accordance with the completion recipe including performing perforation in accordance with the perforation parameters and fracking in accordance with the fracking parameters.

20 Claims, 21 Drawing Sheets

Related U.S. Application Data filed on Jul. 22, 2015, provisional application No. 62/172,735, filed on Jun. 8, 2015.

(51) Int. Cl.

| | | |
|---|---|---|
| *E21B 41/00* | (2006.01) | |
| *E21B 43/26* | (2006.01) | |
| *E21B 43/11* | (2006.01) | |
| *E21B 47/022* | (2012.01) | |
| *E21B 49/00* | (2006.01) | |
| *E21B 43/12* | (2006.01) | |
| *G06N 3/12* | (2006.01) | |
| *G06Q 10/06* | (2012.01) | |
| *G06N 20/00* | (2019.01) | |

(52) U.S. Cl.
CPC ............ *E21B 43/26* (2013.01); *G01V 99/005* (2013.01); *G06N 3/126* (2013.01); *G06N 20/00* (2019.01); *G06Q 10/06375* (2013.01); *E21B 43/12* (2013.01); *E21B 47/022* (2013.01); *E21B 49/00* (2013.01)

(58) Field of Classification Search
CPC ...... E21B 41/0092; E21B 43/11; E21B 43/26; E21B 49/00; E21B 47/022; E21B 43/12
See application file for complete search history.

(56) References Cited

U.S. PATENT DOCUMENTS

| | | |
|---|---|---|
| 6,574,565 B1 | 6/2003 | Bush |
| 6,732,052 B2 | 5/2004 | Macdonald |
| 6,820,702 B2 | 11/2004 | Niedermayr |
| 6,832,159 B2 | 12/2004 | Smits et al. |
| 6,968,909 B2 | 11/2005 | Aldred |
| 7,142,986 B2 | 11/2006 | Moran |
| 7,303,010 B2 | 12/2007 | de Guzman |
| 7,908,230 B2 | 3/2011 | Bailey |
| 7,963,327 B1 | 6/2011 | Saleri et al. |
| 8,121,971 B2 | 2/2012 | Edwards |
| 8,170,800 B2 | 5/2012 | Aamodt |
| 8,209,218 B1 | 6/2012 | Basu et al. |
| 8,364,519 B1 | 1/2013 | Basu et al. |
| 8,474,550 B2 | 7/2013 | Byreddy |
| 8,738,425 B1 | 5/2014 | Basu et al. |
| 9,031,889 B1 | 5/2015 | Basu et al. |
| 9,163,497 B2 | 10/2015 | Laing et al. |
| 9,230,211 B1 | 1/2016 | Basu et al. |
| 9,424,518 B1 | 8/2016 | Basu et al. |
| 9,605,529 B1 | 3/2017 | Venter et al. |
| 9,617,834 B1 | 4/2017 | Venter et al. |
| 9,617,843 B1 | 4/2017 | Venter et al. |
| 9,678,487 B1 | 6/2017 | Basu et al. |
| 9,785,831 B2 | 10/2017 | Takeda et al. |
| 9,836,561 B2 * | 12/2017 | Shen .................. E21B 43/26 |
| 2001/0049595 A1 | 12/2001 | Plumer et al. |
| 2003/0089502 A1 | 5/2003 | Dallas |
| 2004/0133531 A1 | 7/2004 | Chen et al. |
| 2004/0220846 A1 | 11/2004 | Cullick et al. |
| 2005/0192855 A1 | 9/2005 | Chitty et al. |
| 2006/0024171 A1 | 2/2006 | Smith |
| 2007/0289740 A1 * | 12/2007 | Thigpen .................. E21B 37/06 166/250.01 |
| 2008/0183451 A1 | 7/2008 | Weng |
| 2008/0209997 A1 | 9/2008 | Bailey |
| 2008/0281525 A1 | 11/2008 | Boone |
| 2008/0289875 A1 | 11/2008 | Burge |
| 2009/0024443 A1 | 1/2009 | Graham |
| 2009/0125362 A1 | 5/2009 | Reid et al. |
| 2009/0132458 A1 | 5/2009 | Edwards et al. |
| 2009/0157367 A1 | 6/2009 | Meyer |
| 2009/0157590 A1 | 6/2009 | Mijares et al. |
| 2009/0210081 A1 | 8/2009 | Sustaeta |
| 2010/0042458 A1 | 2/2010 | Rashid |
| 2010/0108322 A1 | 5/2010 | Eilertsen |
| 2011/0174541 A1 | 7/2011 | Strachan |
| 2012/0059521 A1 | 3/2012 | Iversen |
| 2012/0116740 A1 | 5/2012 | Fourno et al. |
| 2012/0316787 A1 | 12/2012 | Moran |
| 2013/0116998 A1 | 5/2013 | Shirzadi et al. |
| 2013/0124176 A1 | 5/2013 | Fox |
| 2013/0140031 A1 | 6/2013 | Cohen et al. |
| 2013/0311270 A1 | 11/2013 | Daftary |
| 2014/0067353 A1 * | 3/2014 | Shelley ................ G06N 3/0427 703/10 |
| 2014/0070956 A1 | 3/2014 | Winkler |
| 2014/0297235 A1 | 10/2014 | Arora et al. |
| 2014/0310071 A1 | 10/2014 | Conradson et al. |
| 2014/0365409 A1 | 12/2014 | Burch et al. |
| 2015/0039544 A1 | 2/2015 | Gupta |
| 2015/0053482 A1 | 2/2015 | Boone |
| 2015/0114630 A1 | 4/2015 | Colvin |
| 2015/0186567 A1 | 7/2015 | Wu |
| 2015/0234954 A1 | 8/2015 | Samuel |
| 2015/0278407 A1 | 10/2015 | Vennelakanti et al. |
| 2015/0284811 A1 | 10/2015 | Knight |
| 2015/0300151 A1 | 10/2015 | Mohaghegh |
| 2015/0356403 A1 | 12/2015 | Storm, Jr. |
| 2016/0018562 A1 * | 1/2016 | Bratvedt ................ G06F 17/16 703/2 |
| 2016/0042272 A1 | 2/2016 | Mohaghegh |
| 2016/0063146 A1 * | 3/2016 | Bailey ...................... G06F 17/10 703/2 |
| 2017/0058658 A1 | 3/2017 | Spencer |
| 2017/0286879 A1 | 10/2017 | Yeager |
| 2017/0292362 A1 | 10/2017 | Aniket |
| 2017/0342808 A1 * | 11/2017 | Dykstra .................. E21B 44/00 |
| 2018/0016895 A1 | 1/2018 | Weng et al. |
| 2018/0060744 A1 * | 3/2018 | Achin ................... G06F 9/5011 |
| 2018/0080306 A1 | 3/2018 | Passolt |
| 2019/0249534 A1 * | 8/2019 | Hoeink ................... E21B 41/00 |

OTHER PUBLICATIONS

Ketter et al. "A Field Study in Optimizing Completion Strategies for Fracture Initiation in Barnett Shale Horizontal Wells" SPE 103232 (2008): Society of Petroleum Engineers [retrieved on May 3, 2018]. Retrieved from <https://www.onepetro.org/journal-paper/SPE-103232-PA>.*

Edwards et al. "Marcellus Shale Hydraulic Fracturing and Optimal Well Spacing to Maximize Recovery and Control Costs" SPE 140463 (2011): Society of Petroleum Engineers [retrieved on May 3, 2018]. Retreived from <https://www.onepetro.org/conference-paper/SPE-140463-MS>.*

Economides et al. "Reservoir Stimulation" 3rd Edition (2000): Wiley, Chap 10 [retrieved on May 1, 2018]. Retrieved from <https://www.researchgate.net/profile/Azeez_Aregbe/post/measuring_fracture_length_and_width_using_PKN_and_KGD_models_for_hydraulic_fracturing/attachment/59d64ed379197b80779a8171/AS:494639238529025@1494942593011/download/RS_REF.pdf>.*

Welling et al. "Quantifying the Factors Influencing Gravel Placement and Productivity of an Internally Gravel Packed Completion based on Field Data Analysis" SPE 30113 (1995): Society of Petroleum Engineers [retrieved on May 3, 2018]. Retrieved from <https://www.onepetro.org/conference-paper/SPE-30113-MS>.*

Rahim et al. "Evaluation and Selection of Stimulation Methods in Horizontal Gas Wells for Production Optimization Using Numerical Modeling of Well Performance" SPE 167090 (2013): Society of Petroleum Engineers [retrieved on May 3, 2018]. Retrieved from <https://www.onepetro.org/conference-paper/SPE-167090-MS>.*

Lalehrokh et al. "Well Spacing Optimization in Eagle Ford" SPE 171640-MS (2014): Society of Petroleum Engineers [retrieved on May 3, 2018]. Retrieved from <https://www.onepetro.org/conference-paper/SPE-171640-MS>.*

"Recipe" Merriam-Webster.com [retrieved on May 10, 2018]. Retrieved from <https://www.merriam-webster.com/dictionary/recipe>.*

"Prescribe" Merriam-Webster.com [retrieved on May 9, 2018]. Retrieved from <https://www.merriam-webster.com/dictionary/prescribe>.*

(56) References Cited

OTHER PUBLICATIONS

Sumotarto, U. "Sandstone Acidizing Simulation: Development of an Expert System" ProQuest Dissertations and Theses [retrieved on Feb. 6, 2019]. Retrieved from <https://search.proquest.com/docview/304236236/fulltextPDF/487D9138EE634D17PQ/1?accountid=14753> (Year: 1995).*

Sidahmed et al. "Augmenting Operations Monitoring by Mining Unstructured Drilling Reports" SPE-173429-MS, Mar. 2015, The Woodlands, Texas, USA [retrieved on Feb. 8, 2019]. Retrieved from <https://www.onepetro.org/conference-paper/SPE-173429-MS> (Year: 2015).*

Kravis et al. "A Case Based System for Oil and Gas Well Design with Risk Assessment" Applied Intelligence, vol. 23, pp. 39-53 [retrieved on Feb. 6, 2019]. Retrieved from <https://link.springer.com/content/pdf/10.1007/s10489-005-2371-7.pdf> (Year: 2005).*

Irrgang et al. "Drilling Knowledge Management, What is Missing and Can We Fix it?" IADC/SPE 77249, IADC/SPE Asia Pacific Drilling Technology, Jakarata, Indonesia [retrieved on Feb. 8, 2019]. Retrieved from <https://www.onepetro.org/conference-paper/SPE-77249-MS> (Year: 2002).*

Centilmen et al. "Applications of Neural Networks in Multiwell Field Development" Applications of Neural Networks in Multiwell Field Development, SPE 56433, pp. 1-11 [retrieved on Sep. 7, 2019]. Retrieved from <https://www.onepetro.org/download/conference-paper/SPE-56433-MS> (Year: 1999).*

Denil et al. "Predicting Parameters in Deep Learning" v.2, Cornell University; arXiv:1306.0543 [retrieved on Sep. 9, 2019]. Retrieved from <https://arxiv.org/abs/1306.0543> (Year: 2014).*

Parada et al. "A New Screening Tool for Improved Oil Recovery Methods Using Artificial Neural Networks" Society of Petroleum Engineers, SPE 153321, pp. 1-17 [retrieved on Sep. 7, 2019]. Retrieved from <https://www.onepetro.org/conference-paper/SPE-153321-MS> (Year: 2012).*

Holdaway et al. "Drilling Optimization in Unconventional and Tight Gas Fields: An Innovative Approach" SPE Middle East Unconventional Gas Conference and Exhibition, SPE 142509, pp. 1-19 [retrieved on Sep. 9, 2019]. Retrieved from <https://www.onepetro.org/conference-paper/SPE-142509-MS> (Year: 2011).*

Ramgulam et al. "Utilization of Artificial Neural Networks in the Optimization of History Matching" SPE Latin American and Caribbean Petroleum Engineering Conference, SPE 107468, pp. 1-15 [retrieved on Sep. 7, 2019]. Retrieved from <https://www.onepetro.org/download/conference-paper/SPE-107468-MS> (Year: 2007).*

Kyte et al. "Horizontal Spacing, Depletion, and Infill Potential in the Austin Chalk" SPE Annual Technical Conference and Exhibition, SPE 36721, pp. 409-415 [retrieved on Sep. 7, 2019]. Retrieved from <https://www.onepetro.org/download/conference-paper/SPE-36721-MS?id=conference-paper%2FSPE-36721-MS> (Year: 1996).*

Baan et al. "Neural networks in geophysical applications" Geophysics, vol. 65, No. 4, pp. 1032-1047 [retrieved on Sep. 9, 2019]. Retrieved from <http://eprints.whiterose.ac.uk/325/1/vanderBaanm2.pdf> (Year: 2000).*

Can et al. "Probabilistic Production Forecasting for Unconventional Reservoirs with Stretched Exponential Production Decline Model" SPE Reservoir Evaluation and Engineering, pp. 41-50 [retrieved on Sep. 9, 2019]. Retrieved from <> (Year: 2012).*

Cambridge Dictionary (engine): Cambridge University Press [retrieved on Oct. 19, 2018]. Retrieved from <https://dictionary.cambridge.org/us/dictionary/english/engine> (Year: 2018).

Dursun et al. "A Workflow for Intelligent Data-Driven Analytics Software Development in Oil and Gas Industry" SPE-170859-MS, Society of Petroleum Engineers [retrieved on Oct. 20, 2018]. Retrieved from <https://www.onepetro.org/conference-paper/SPE-170859-MS?event-fire=false> (Year: 2014).

Singh, S. "How are Oil Well Drilling Companies Using Analytics" Analytics and Big Data [blog post] : Genpact [retrieved on Oct. 20, 2018]. Retrieved from <https://www.genpact.com/insight/blog/how-are-oil-well-drilling-companies-using-analytics-to-drive-productivity-and-the-return-on-assets> (Year: 2015).

Johnston et al. "New Findings in Drilling and Wells using Big Data Analytics" OTC-26021-MS, Offshore Technology Conference [retrieved on Oct. 20, 2018]. Retrieved from <https://www.onepetro.org/conference-paper/OTC-26021-MS> (Year: 2015).

"How do we improve drilling efficiency and predict events" Oil and Gas, [Solution Brief]: SAS [retrieved on Oct. 20, 2018]. Retrieved from <https://web.archive.org/web/20150919235922/https://www.sas.com/content/darn/SAS/en us/doc/solutionbrief/ oil-and-gas-improve-drilling-efficiency-106477.pdf> (Year: 2015).

Austin, E.H. "Drilling Engineering Handbook." (1984). (Year: 1984).

U.S. Appl. No. 16/146,590, filed Sep. 28, 2018.

Yusof et al. "Development of mathematical model for hydraulic fracturing design" Journal of Petroleum Exploration and Production Technologym vol. 5, Iss. 3, pp. 269-276 [retrieved on May 2, 2018]. Retrieved from <https://link.springer.com/article/10.1007/s13202-014-0124-z> (Year: 2014).

Hastie, Travor, Robert Tibshirani, and Jerome Friedman. "The elements of statistical learning: data mining, inference, and prediction, Springer Series in Statistics." (2009): 219:260 (Year: 2009).

"Date" Merriam-Webster.com [downloaded May 8, 2018]; https://www.merriam-webster.com/dictionary/date.

"Field", Merriam-Webster.com [downloaded Apr. 26, 2018]; https://www.merriam-webster.com/dictionary/field.

Babaniyazov et al. "Methodological Approach for Optimization of Completion Practices in Mature Carbonate Fields" SPE 166249 (2013); Society of Petroleum Engineers [downloaded May 1, 2018]; https://www.onepetro.org/conferencepaper/SPE-166249-MS.

Butler, R. "Steam and Gas Push (SAGP)" 48th Annual Technical Meeting of the Petroleum Society (1997); Alberta, Canada [downloaded Mar. 28, 2018] https://www.onepetro.org/conference-paper/PETSOC-97-137.

Clegg, J. D. et al., Recommendations and Comparisons for Selecting Artificial-Lift Methods (includes associated papers 28645 and 29092); Journal of Petroleum Technology 45.12 (Dec. 1993 and Jul. 1994); pp. 1128-1167 and pp. 621-622.

Devoid, Havard; Oil and gas production handbook: an introduction to oil and gas production. Lulu. com, 2013; pp. 1-8, 33-36, 80-82, 102-104.

Schlumberger, "FracCADE Stimulation Proposal" Example 8: (2013) [downloaded May 1, 2018]; http://ocdimage.emnrd.state.nm.us/imaging/filestore/SantaFeAdmin/CF/259053/15235_13_CF.pdf.

Teichrob et al. "Well Construction Optimization in the Motney Formation in the Karr Kakwa Area of Central Western Alberta: A Case Study" SPE 162734 (2012) [downloaded Mar. 20, 2018], https://www.onepetro.org/conference-paper/SPE162734-MS.

Rizzo et al., "An Ontology Based for Drilling Report Classification," Springer-Verlag Berlin Heidelberg (2006).

Serapiao et al., "Classification of Petroleum Well Drilling Operations Using Support Vector Machine (SVM)," IEEE (2006).

U.S. Appl. No. 15/052,567, filed Feb. 24, 2016.
U.S. Appl. No. 15/052,546, filed Feb. 24, 2016.
U.S. Appl. No. 15/052,559, filed Feb. 24, 2016.
U.S. Appl. No. 15/052,579, filed Feb. 24, 2016.
U.S. Appl. No. 15/052,608, filed Feb. 24, 2016.
U.S. Appl. No. 15/052,634, filed Feb. 24, 2016.
U.S. Appl. No. 15/052,646, filed Feb. 24, 2016.
U.S. Appl. No. 15/052,653, filed Feb. 24, 2016.
U.S. Appl. No. 15/052,658, filed Feb. 24, 2016.
U.S. Appl. No. 15/052,660, filed Feb. 24, 2016.
U.S. Appl. No. 15/052,667, filed Feb. 24, 2016.

Bansal, "Forecasting the Production Performance of Wells Located in Tight Oil Plays Using Artificial Expert Systems," Pennsylvania State University Graduate School, John and Willie Leone Family Department of Energy and Mineral Engineering, Dec. 2011.

Ma, "Practical Implementation of Knowledge-Based Approaches for SAGD Production and Analysis," SPE Heavy Oil Conference, Canada, SPE-170144-MS.

* cited by examiner

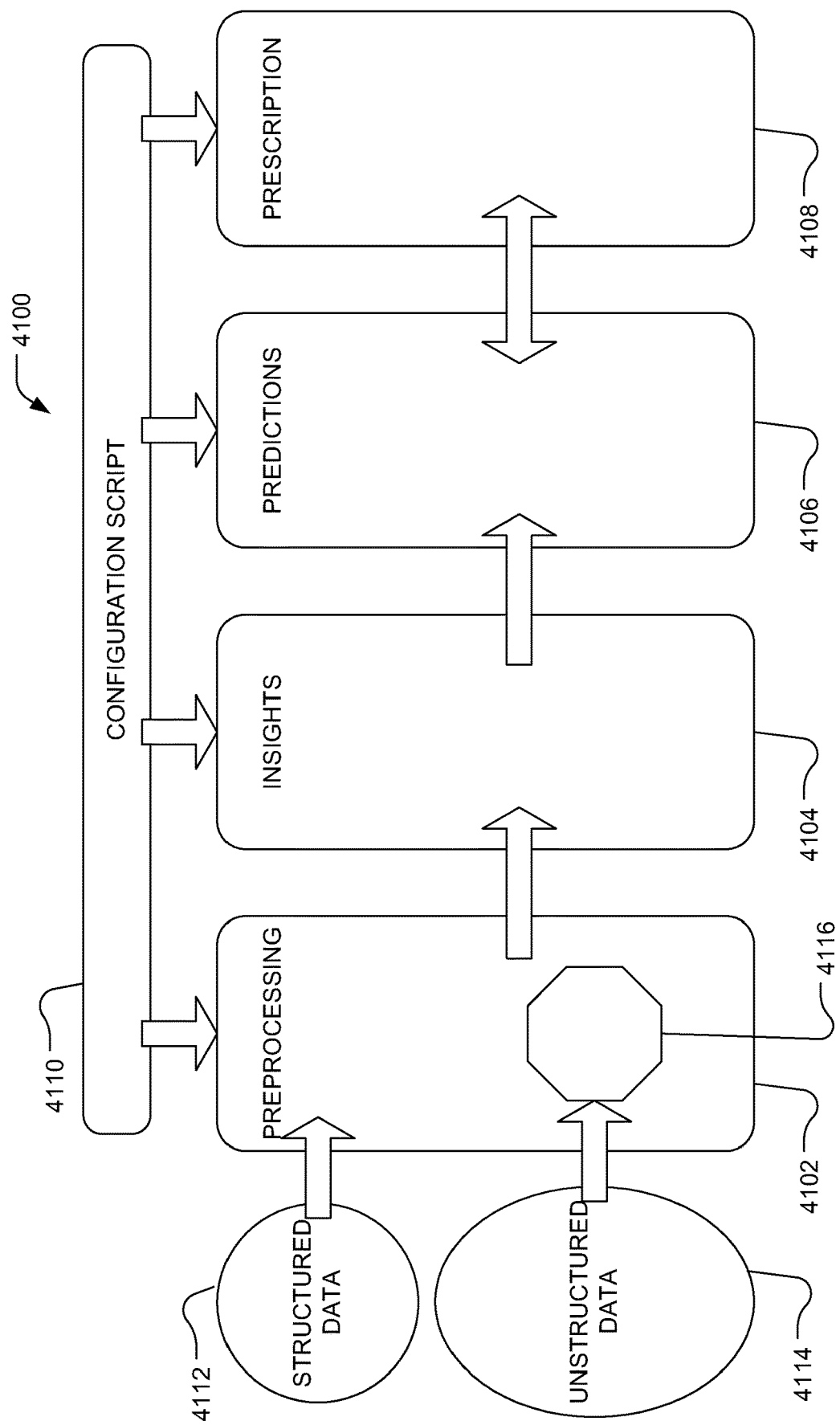

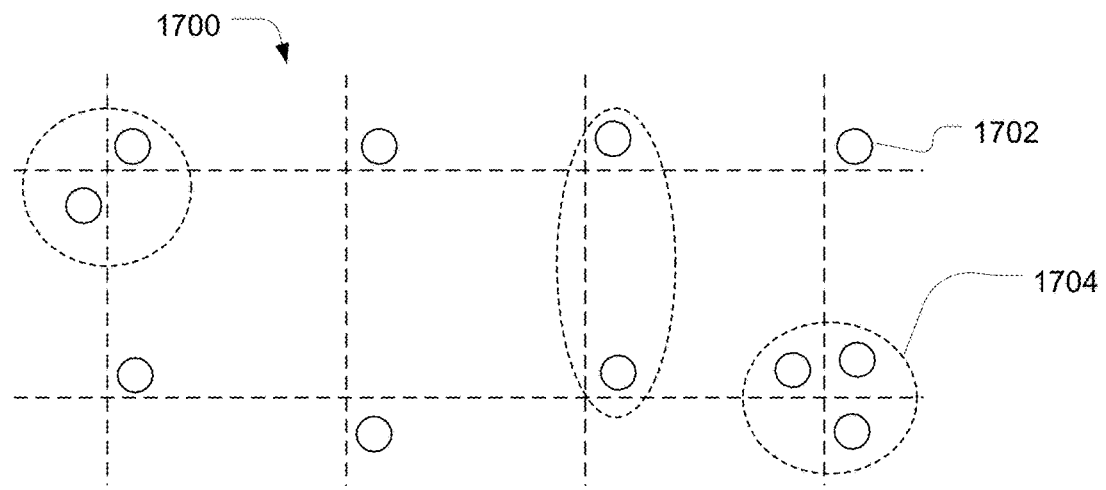
FIG. 17
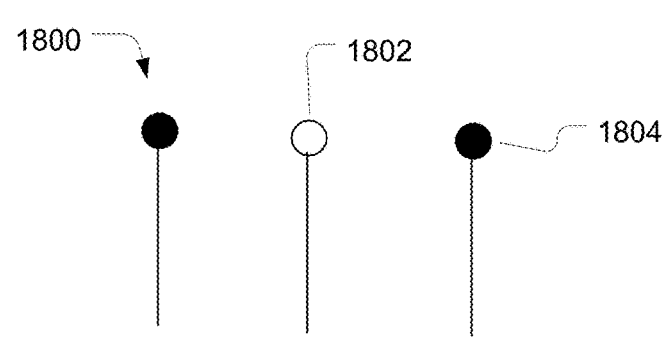
FIG. 18
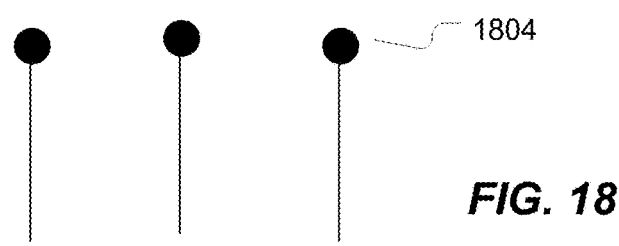
FIG. 19
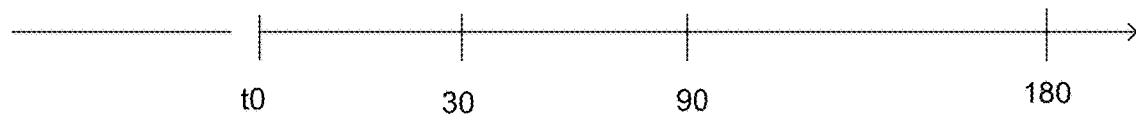

Before

After

SYSTEMS AND METHODS FOR ANALYZING RESOURCE PRODUCTION

CROSS-REFERENCE TO RELATED APPLICATION(S)

This application claims benefit of U.S. Provisional Application No. 62/172,735, entitled "SYSTEMS AND METHODS FOR ANALYZING RESOURCE PRODUCTION," filed Jun. 8, 2015, which is incorporated herein by reference in its entirety.

This application claims benefit of U.S. Provisional Application No. 62/195,775, entitled "SYSTEMS AND METHODS FOR ANALYZING RESOURCE PRODUCTION," filed Jul. 22, 2015, which is incorporated herein by reference in its entirety.

This application claims benefit of U.S. Provisional Application No. 62/246,121, entitled "SYSTEMS AND METHODS FOR ANALYZING RESOURCE PRODUCTION," filed Oct. 25, 2015, which is incorporated herein by reference in its entirety.

FIELD OF THE DISCLOSURE

This disclosure, in general, relates to systems and methods for performing data analysis, prediction, and prescription using scripting.

BACKGROUND

Industry is increasingly relying on analytics and prediction systems to predict events and business outcomes. With these predictions, businesses hope to preempt problems and improve business performance. However, such analytics systems are becoming increasingly complex, limiting usability by managers.

In particular, subprocesses within the analytics system, such as data preprocessing and modeling, utilize complex algorithms and techniques, each using a variety of parameters and factors that influence functionality. For example, industry is increasingly turning to unstructured data sources that are preprocessed using a variety of interpreters and algorithms, each utilizing a different set of parameters and providing a different output.

As such, the complexity of conventional analytics systems often prevents use of such systems by business management. Further, the expense associated with using expert labor to perform analysis and yield predictions leads to less frequent use and lowers the cost effectiveness of such systems.

In particular, such systems have can have use in resource management, such as oil field management, and other production-based industries.

BRIEF DESCRIPTION OF THE DRAWINGS

The present disclosure may be better understood, and its numerous features and advantages made apparent to those skilled in the art by referencing the accompanying drawings.

FIG. 10 and FIG. 11 include illustrations of exemplary analytics systems.

FIG. 17 and FIG. 18 include illustrations of exemplary oil fields.

FIG. 19 includes a time line of production.

The use of the same reference symbols in different drawings indicates similar or identical items.

DETAILED DESCRIPTION

Figure 1:
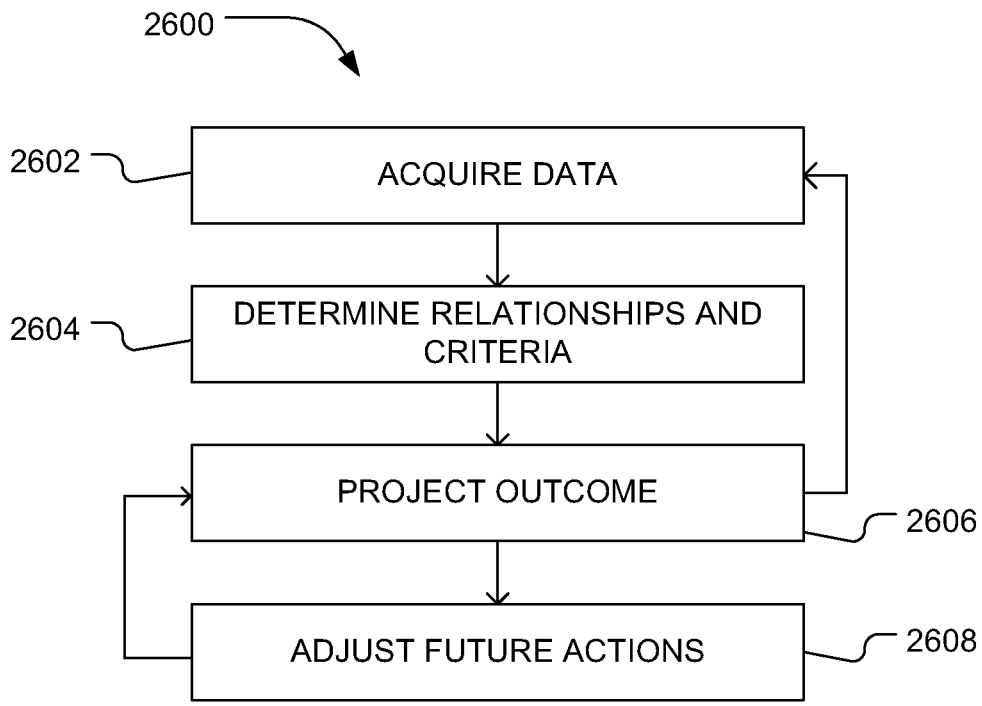
FIG. 1 includes a flow diagram illustrating an exemplary process.

In an embodiment, an analytics system includes several subsystems and a configuration script to configure aspects of the subsystems. The subsystems can include a preprocessing subsystem, an insight or modeling subsystem, a prediction subsystem, a prescription subsystem, or a combination thereof. The configuration script can include elements relevant to the configuration of several of the subsystems and can include elements to specifically configure individual subsystems. In an example, the configuration script can identify variables, such as influencers and performance indicators, used by several of the subsystems. In addition, the configuration script can identify specific parameters, processes, or data useful by a particular subsystem. Such an analytics system is particularly adapted for Prescriptive Analytics® techniques. In particular, such an analytic system can be used to prescribe actions, such as actions at future times useful for achieving performance goals. Further, associated methods and systems can be used to provide a Decision-as-a-Service™ software and online services to assist business entities achieve a desired performance.

In particular, the analytics system and methods can be used to implement Prescriptive Analytics® techniques that assist with determining future actions or decisions in view of business rules and projected outcomes. The methods can be embodied in executable instructions, processors or systems to execute such instructions, interfaces implemented by such systems, media storing such executable instructions, and services derived from the use of such methods and systems. In addition, the methods can be utilized to provide Predictive Decision Management® information and services, such as Decision-as-a-Service™ services. In particular, the methods can implement predictive analysis, such as forecasting to project what will happen and when. Further, the methods can implement optimization, scenario testing, and root cause analysis of factors that influence performance.

In an embodiment, a system predicts problems that can occur, providing an indication of both the nature of the problem and when it is expected to occur. The problems can be expressed as deviations in performance indicators that violate business criteria. For example, a problem can be expressed as the value of a performance indicator crossing a threshold. In addition, the system supports testing of solutions to the predicted problem. The solutions are expressed in terms of what action to take and when to take such action. As such, the system assists with determining a desirable set of future actions to maintain a business process in compliance with business criteria. Deviations from performance indicators that violate business criteria can also include opportunities from which the business can benefit. For example, when a future customer satisfaction score exceeds a threshold, the business can decide to reduce its service level and thus, reduce cost.

Businesses rely on business processes to function. Evaluating how well that business process is performing allows a business to allocate resources, increase production, improve its position in the market place, increase profitability, or any combination thereof. For example, a business process can include a call center, the function being customer service or technical support. In another example, the business process can include field services, the function being product installation or repair. In a further example, the business process can be a marketing department, the function being to control public perception of the business or a response rate. In additional examples, the business process can include transactions services, finance and accounting, manufacturing, logistics, sales, or any combination thereof.

In particular, evaluation of the business process can be correlated with performance indicators (PIs). One or more performance indicators (PIs) can be used to quantify how well a business process is performing. For example, a call center can quantify performance using performance indicators, such as customer satisfaction, problem resolution, productivity indicators, cost indicators, or any combination thereof.

Once determined, the performance indicators (PIs) can be compared with business criteria to determine whether the business process is performing as desired. For example, a business criterion can include threshold values, limits on rates of change, heuristics associated with aspects of the business function or any combination thereof. For example, the performance indicator (PI) can be compared to a threshold value to determine whether the performance indicator (PI) is within a desired range or is in violation of the threshold, indicating poor performance or an unnecessary high performance.

The performance indicators (PIs) are influenced by other factors associated with performing the business process. In particular, such factors are referred to as influencers and influencers correlate with the performance indicators. For example, an influencer associated with call center performance can include the number of contacts made with a customer to resolve an issue, the type of issue, hold time, shipping delays, or any combination thereof, among others.

Such influencers can, for example, influence performance indicators, such as customer satisfaction and brand satisfaction. Performance indicators (PIs) or influencers can be of numerical (continuous or integer) nature, categorical nature, or a combination thereof. Further, the PIs or influencers can be ordered or can be non-ordered. In another example, the distributions of performance indicators (PIs) or influencers are utilized or predicted. In particular, a PI distribution provides data about the underlying nature of the median or mean value. For example, when the PI relates to customer satisfaction, an average value does not provide information about the number of dissatisfied customers. An average of 80% satisfaction can be the result of all participants having a satisfaction near 80% or can be the result of several 100% satisfied customers and a few very dissatisfied customers. Identifying the existence and then cause of the few very dissatisfied customers can provide greater benefit than seeking to achieve an average value. In the case of categorical performance indicators (PIs) or influencers, such a prediction can include the prediction of the occurrence set of categories. As used below, the term "value" is used to include numerical values, categorical values, or any combination thereof.

The influencers and the performance indicators (PIs) change over time. The change can be caused by the change of influencers or by a time dependency of a performance indicator on itself. As such, the performance indicator (PI) can deviate overtime and violate business criteria, which is indicative of a problem in the business unit or low performance. To correct the deviation, associated influencers can be manipulated. For example, more staff can be added to reduce hold time. However, immediate manipulation of the influencers to solve a problem predicted in the future can provide less than desirable solutions to the problems in the business process. For example, hiring more staff long before the hold times are expected to increase leads to higher cost in the call center. The present system can assists with determining a desirable set of future actions to maintain a business process incompliance with business criteria.

In an embodiment, the present system performs a method to determine such a desirable set of future actions. For example, FIG. 1 illustrates a method 2600, which includes acquiring data (2602), determining relationships and criteria (2604), predicting outcomes (2606) and adjusting future actions (2608). The present system can acquire data, as illustrated at 2602, from a variety of sources. The data can be acquired from external sources. Exemplary external sources include databases, customer service logs, surveys, testing, or any combination thereof, among others. In particular, the data can be derived from structured sources. In another example, the data can be derived from unstructured sources. The data can be transformed and aggregated. In addition, the data can be cleaned. The resulting data can be stored in a data management system.

In an example, the system can also use streaming data sources where there is no intermediate data management system for the storage of aggregated data. Such a system is especially useful for big unstructured data sets (terabyte data) where the use of a rational database management system would be inefficient or economically unacceptable. In such an example, techniques such as Map/Reduce are applied based on Big Data processing systems like Apache Hadoop.

Once clean aggregated data is available, relationships between performance indicators and potential influencers can be determined and criteria for performance can be established, as illustrated at 2604. Such relationships permit projection of potential outcomes, which can be compared with the criteria to determine whether the business process is functioning well. In particular, the relationships can identify influencers that have a greater influence on one or more performance indicators.

As illustrated at 2606, outcomes can be projected. Projecting can include predictive analysis to determine what is to happen. Predictive analysis can include forecasting to determine what is to happen and in what time frame. In particular, such projection can include projecting the value of one or more performance indicators based on the determined relationships and expected values of influencers. In a further example, the future values of one or more influencers are projected, and the performance indicators are determined based at least in part on the future values of the one or more influencers. Projecting, and in particular, forecasting can be performed using an algorithm constrained with business rules. For example, the values of influencers or performance indicators can be constrained based on rules established by the business. In an example, one or more of the performance indicators are projected to violate one or more business criteria at future times. For example, the value of a performance indicator can cross a threshold at a future time step. In this way, the business process is provided with warning about a potential problem that may arise in the future.

The present system can also permit adjustment of future actions, as illustrated at 2608. For example, to determine a solution to a projected problem, the system can adjust, in an automatic mode or through manual adjustment, the future value of one or more influencers. The performance indicators can be projected using the adjusted influencer values to determine whether the problem is solved. In particular, the adjustment to influencer values can be made at one or more future time steps. As such, minor adjustments to an influencer value can be made during a series of time steps. In another example, a large adjustment can be made at a single time step closer to the projected violation of the business criteria. The process can be iterated to determine a particularly advantageous set of future actions that maintain the performance indicators at desired states. In particular, a performance indicator can be optimized by adjusting one or more values of the influencers. As used herein, optimizing is a process of adjusting values to meet or approach a criterion. Further, the process can be constrained based on business rules. For example, business rules can set boundaries to the values of influencers or performance indicators.

In addition, the future actions and data derived therefrom can be used to recalibrate the system. For example, new results relating actions taken can be used to inform the algorithm and for selection of an algorithm. Other processes, such as iteratively adjusting or optimizing or root cause analysis, can be performed automatically or continuously in response to new data.

Figure 2:
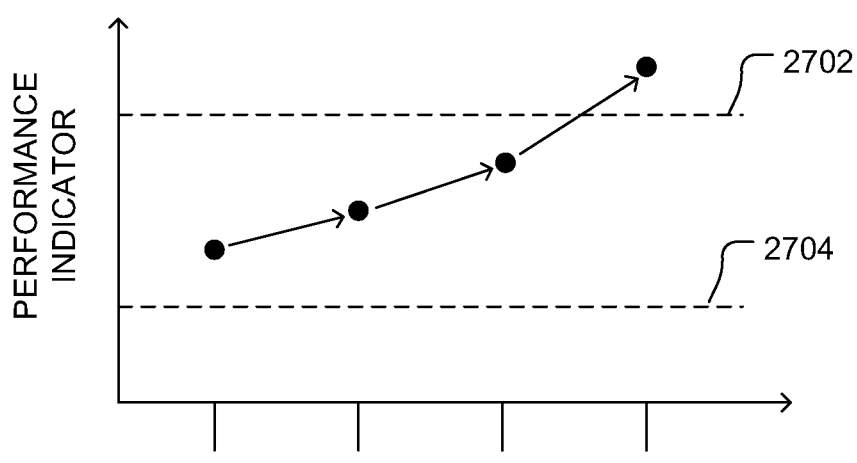
FIG. 2 includes a graph illustration of an exemplary relationship between a performance indicator and time.

To conceptually illustrate the iterations to determine a desirable set of future actions to maintain a business process in compliance with business criteria, FIG. 2 includes a graph illustration of the relationship between the value of a performance indicator and time. As illustrated, with each step in time, the value of the performance indicator changes. At the fourth time step, the value of the performance indicator violates a business criterion. The business criterion is illustrated as a threshold 2702. When the value of the performance indicator extends above the threshold 2702 or is below the threshold 2704, the performance indicator has violated business criteria. Alternatively, the business criteria can be expressed as limits to a rate of change. In another example, the thresholds can have difference values at different times.

Figure 3:
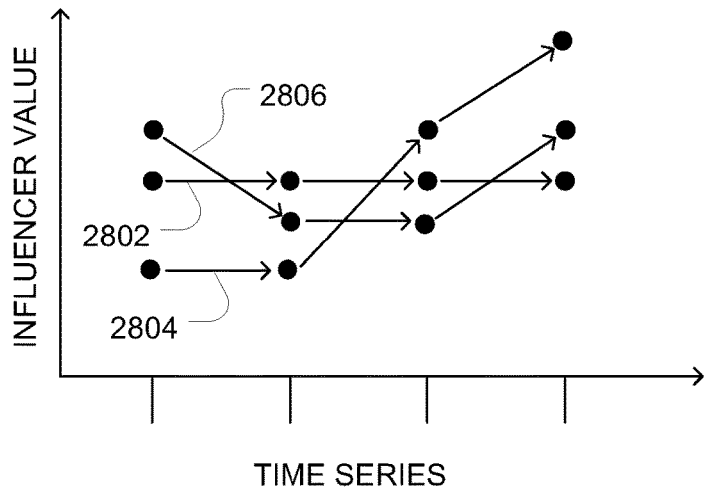
FIG. 3 includes a graph illustration of exemplary relationships between the value of influencers and time.

FIG. 3 illustrates expected influencer values over time. To more easily visualize a comparison, the values can be normalized. While a multiline chart is used to illustrate FIG. 3 for conceptual purposes, the influencer values can include categorical values, numerical values, or any combination thereof. For example, an influencer 2802 can have constant values at each of a series of time steps. In another example, an influencer 2804 can have values that increase with each subsequent time step. Alternatively, the value of an influencer can fluctuate with each time step. For example, an influencer 2806 can decrease in a first time step and increase at a subsequent time step. While the values of three exemplary influencers are illustrated, influencer values can be projected to increase, decrease, or remain the same with each time step in the time series.

In particular, the influencer values or categories can be projected based on known factors and prior history. For example, if call volume or hold time are considered influencers of customer satisfaction in a call center, it may be projected, based on past experience, that call volume and hold time increase during holiday seasons. In a field service process for a heating and air conditioning company, service calls can increase during summer months in Southern regions and increase in winter months in Northern regions. As such, embodiments of the present system can utilize manually set values of influencers, projected values of influencers, or any combination thereof.

Figure 4:
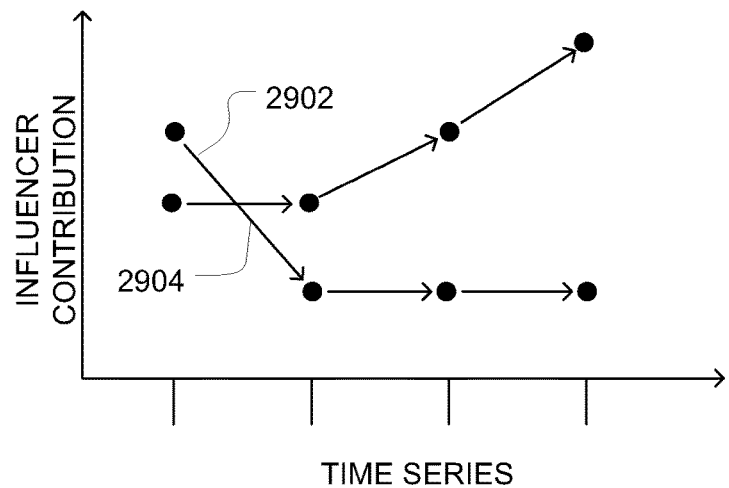
FIG. 4 includes a graph illustration of exemplary relationships between time and the contribution of an influencer to the value of a performance indicator.

Each influencer can contribute to the projected value of one or more performance indicators and each performance indicator can be a function of one or more influencers and time. In particular, determining the relationship of influencers and performance indicators includes determining the contribution of each influencer to the value of a projected performance parameter. Such conceptual contributions are in practice a model derived from data and relevant algorithms. FIG. 4 illustrates conceptually the contribution of two influencers to a projected performance indicator. In addition to the value of the influencer, the value of the performance indicator can be influenced by how much a particular influencer influences the value of the performance indicator at future time steps. For example, the contribution of an influencer 2902 to the value of a performance indicator can decrease over time. As illustrated, the value of influencer 2902 contributes significantly to the current value of the performance indicator. However, the value of the influencer 2902 contributes less to projected values of the performance indicator. In such an example, the influencer 2902 may not correlate with future values of the performance indicator. In contrast, the contribution of an influencer 2904 to the value of a performance indicator increases at subsequent time steps. For example, the value of the influencer 2904 can correlate strongly with the value of the performance indicator at a future time step.

Using the influencer values or categories, whether projected or manually set, and using the relationships of such influencer values or categories on future values of the performance indicator, the system can project performance indicator values or categories over a series of future time steps and iteratively adjust the influencer values or the occurrence of categories at future time steps to determine desirable changes to influencer values or categories at future time steps that maintain the performance indicators in balance with the business criteria.

Figure 5:
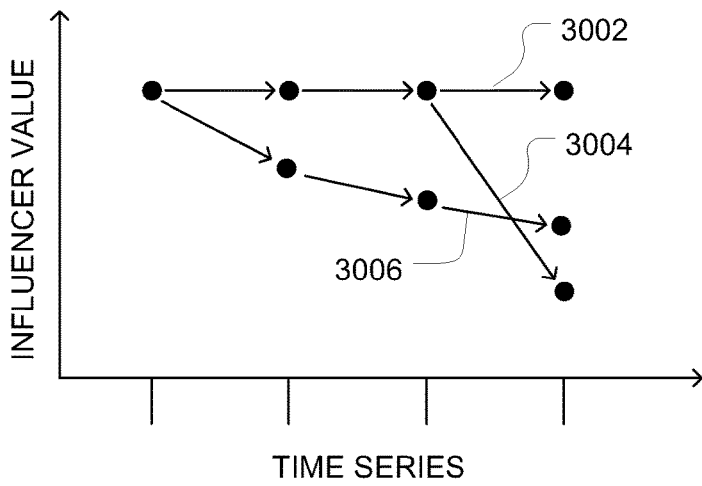
FIG. 5 includes a graph illustration of exemplary changes to the value of an influencer projected over time.

For example, FIG. 5 includes an illustration of sets of changes that can be made to the values of an influencer through a time series. In an example, the value of the influencer can be constant through time, as illustrated at 3002. Such a path (set of consecutive values of an influencer) can lead to a violation of a business criterion by performance indicators. To prevent violation of the business criterion, the influencer can be decreased at at least one future time step. For example, at a third time step the influencer can be reduced significantly, as illustrated at 3004, to prevent a violation. In another example, the influencer can be gradually reduced over a series of time steps, as illustrated at 3006. As such, different paths or sets of changes to an influencer value can be assessed to determine a preferred path that maintains the business process in compliance. In an example, such a path can be preferred because it is a lower cost solution or has advantages not present with other paths.

As such, embodiments of the present system can assist with determining a set of future actions (changes to influencers) that maintain a business process, as quantified by performance indicators, in compliance with business criteria. In other words, the present system can assist with determining which changes to make to a business process and when to make such changes.

Figure 6:
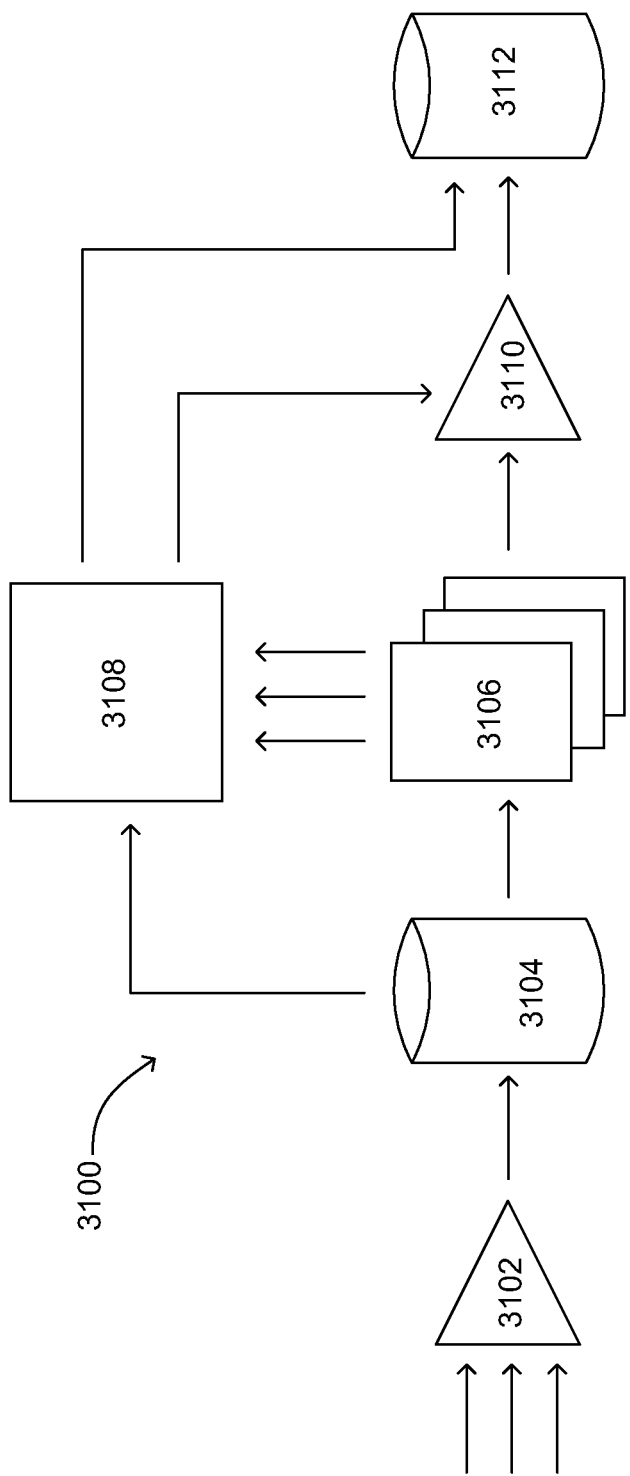
FIG. 6 includes an illustration of an exemplary process for predictive decision making.

In an embodiment illustrated in FIG. 6, a system 3100 includes tools 3102 for processing raw data gathered from external sources. For example, the tools 3102 can assist with loading data from external sources, transforming the data into desirable formats, aggregating the data, and cleaning the data.

In particular, the data can be derived from structured sources, such as databases, tables, listings, or any combination thereof. In another example, the data can be derived from unstructured sources. Unstructured sources are sources that are interpreted using human or artificial intelligence and, for example, include video sources, audio sources, narrative text, or any combination thereof. Narrative text includes, for example, articles, blogs, emails, and other writings in prose, such as those available via the internet or electronic sources. Further, unstructured sources can include documents having narrative text and including enriched formatting, such as tags. For example, the unstructured source can include a narrative text document formulated in a hypertext, XML or tagged format. Once processed, the data is stored, for example, in a data management system, such as a database 3104.

The data and a set of algorithms 3106 can be used to prepare models. Algorithms 3106 can take the form of heuristics or the form of algorithms to form regression models, Markov chains, time series models, state space models, Bayesian models, neural networks, or any other appropriate model, or any combination thereof. In particular, exemplary algorithms 3106 include autoregressive integrated moving average (ARIMA), seasonal ARIMA (SARIMA), autoregressive conditional heteroskedasticity (ARCH), or generalized autoregressive conditional heteroskedasticity (GARCH), among others. The data can be applied though the algorithms 3106 to provide relationships and models between influencers and performance indicators, which can be validated against a test set from the original data, at validation 3108. Validation 3108 results can be used by selector 3110 to select a preferred model 3106. The model is assembled and stored in a model management system 3112, through which performance indicators can be projected and desirable paths of influencer values determined.

Once prepared, embodiments of the present system can apply new external data, in addition to existing data, to project the values of influencers and performance indicators. A user can configure the system, establishing, for example, a period over which projects are to be made, and other parameters associated with the system. In addition, embodiments of the system can assist with ranking a set of influencers based on their contribution to a particular performance indicator. A small change in a high ranking influencer can have a greater effect on a performance indicator than a large change in a low ranking influencer. Such a ranking can be used to perform root cause analysis. Further, the system can be tested for accuracy based on the model. The ranking can be displayed on a display device.

Figure 7:
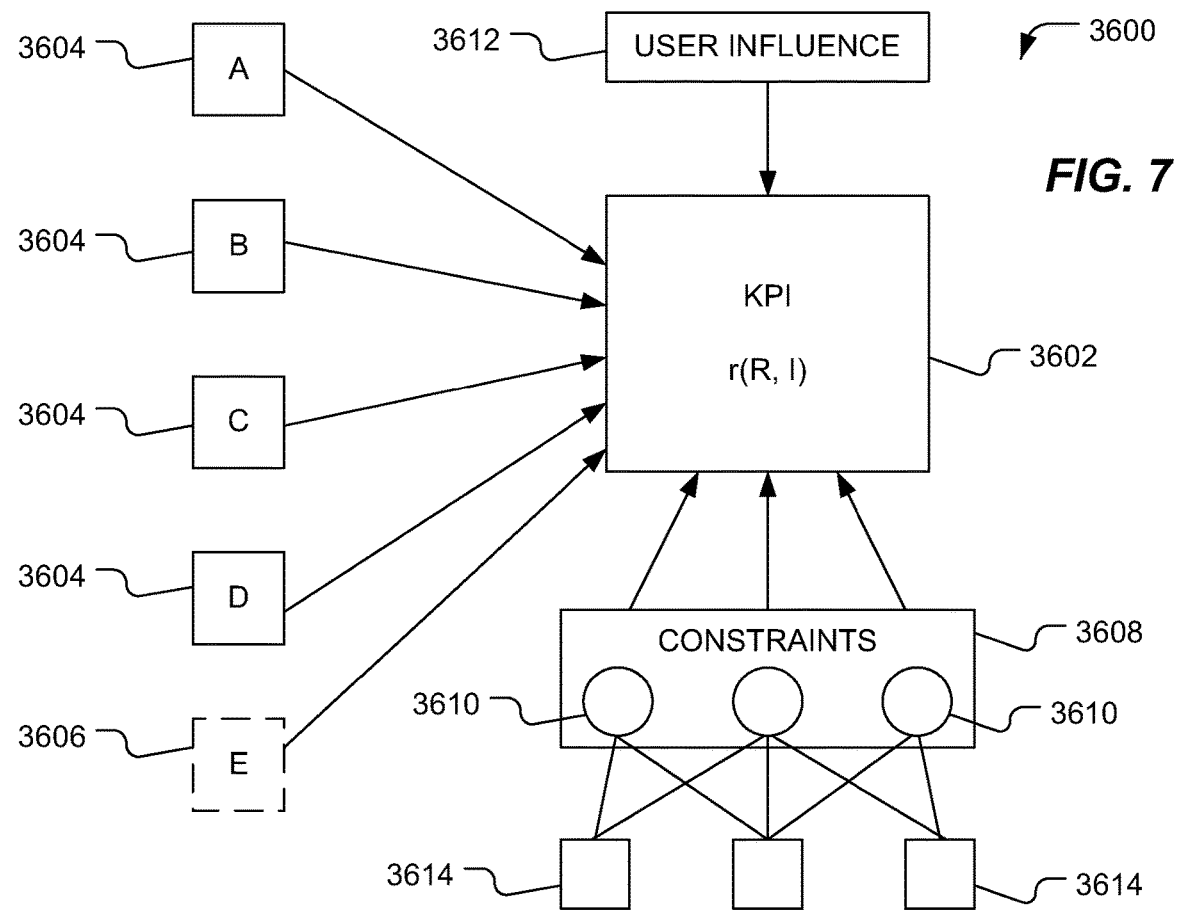
FIG. 7 and FIG. 8 include illustrations of exemplary methods for determining key performance indicator values.

In further explanation of a system 3600, key performance indicators 3602 are influenced by influencers 3604 as constrained by constraints 3608, as illustrated in FIG. 7. Further, a user 3612 can influence the relationships established between constraints (R) and influencers (I). For example, a user can select parameters, a type of model, or other factors that influence how a relationship (r) is established between the influencers 3604, the constraints 3608, and the KPI 3602. In an example, the user 3612 can influence the system through a user interface or by using a configuration script.

Such a relationship (r) permits the determination of the KPI 3602 at one or more future time periods based on present and future values of influencers 3604 subject to constraints 3608. In addition, such a relationship (r) is useful for determining the influence of changes in the influencers 3604 on the KPI 3602 at a selected future time. As a result, root cause analysis can be performed specifically for the selected future time or generally across time periods. In addition, the system can automatically or iteratively determine a set of actionable tasks including changes to influencer values over time to provide future KPI values 3602 that do not violate business rules, subject to constraints 3608. A business rule can be a constraint. Alternatively, a business rule can be different than a constraint. In a further example, a user can manipulate one or more future values of a selected influencer 3604 to determine the effect on the future value of a key performance indicator.

The constraints 3608 can take a variety of forms including box constraints, functional constraints, quantized constraints, step constraints or any combination thereof. The constraint may not be static over time. In particular, the system can indicate that a constraint is to be changed based on auxiliary data. As a result, a constraint can evolve over time, providing an indication of new business rules or a new paradigm discovered through data provided to the system. For example, a range associated with a box constraint can be changed when a value of the KPI or an influencer is frequently in violation of limits of a box constraint. Such sticking to an upper or lower constraint can indicate that a more optimal solution is found in a different range of the influencer value. When the constraint is a function, the form of the function or the parameters associated with the function can change over time as data is provided to the system. Such constraints can also be a relationship based on business rules and performance indicators. In an additional example, a constraint can limit the range of an associated influencer based on the temporally adjacent values of the associated influencer. In an example, constraints 3610 are each influenced by external data 3614. As external data is provided to the constraints 3610, constraints can change or can provide a user with an indication that the constraint should be reconsidered. In such a manner, new business rules can be discovered, preconceived notions of doing business can be reevaluated, and adjustments to the constraints can be considered.

Determining whether to change a constraint or other rules within the system can be performed utilizing meta-rules. Meta-rules can apply a generalize rule to constraints based on the type of constraint or the behavior of data associated with the constraint. For example, when a prescribed influencer is at the top or the bottom of a box constraint for a set number of times, the system can indicate that the constraint should be reconsidered. In another example, when an influencer exhibits erratic changes providing a high variance in influencer values, the absence of a constraint or a preference for reconsidering constraints can be indicated. In such a manner, business rules and other constraints can be adaptive, compensating for changes in a business environment.

In a further example, analysis by user 3612 can influence the nature of the relationship. Using techniques, such as Bayesian networks, can indicate whether additional influencers should be included in the relationship (r). For example, analysis of the system can indicate that an additional influencer 3606 should be provided to establish a relationship (r) for determining future KPI values. As such, the system can assist with building a relationship model, selecting appropriate influencers, and introducing or removing influencers as a business environment changes or the influencers lose influence on the KPI.

Figure 8:
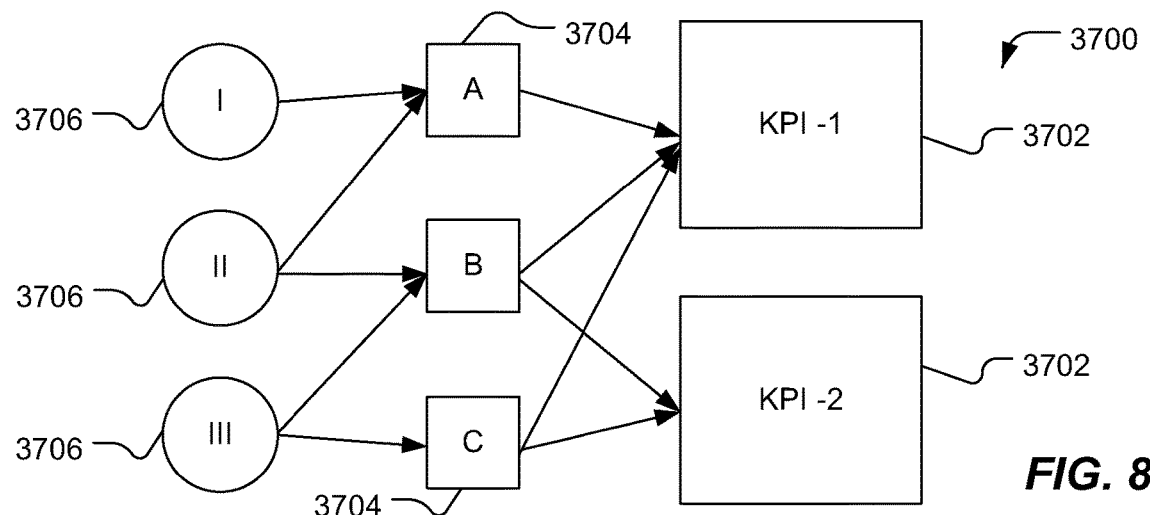

Such networks can be further utilized to translate actions 3706 into influencers 3704 that are used in relational models to determine values of the performance indicators 3702, as illustrated at FIG. 8. In particular, exemplary action hierarchies can combine user actions 3706 into differing influencers 3704 that provide relationships for determining future values of key performance indicators. In this way, the system 3700 can provide a way of translating actionable business actions to future values of key performance indicators using intermediary influencer values. When influencer values are determined for a future actionable pathway, actions 3706 can be determined from influencers 3704 and implemented by a user.

The future value of an influencer can also be limited by values of temporally neighboring future values. For example, an influencer at a first future time can limit the value of the influencer at a second future time. Such a limit can be expressed based on step limits (e.g., maximum permissible change). In another example, the limit can be expressed as a function of time. For example, limits on the value of an influencer can change based on time, either relative or according to a calendar.

When limits to influencer values are a function of time or other influencer values, optimization to achieve a desired key performance indicator value can take longer to implement. Limits to influencer or indicator values that are a function of time or other influencer or indicator values are referred to herein as "functors." For example, when an influencer value is functionally constrained based on time, changing the value of the influencer to a substantially optimal value can be prevented until the functional constraint permits the influencer to have the substantially optimal value.

In a further example, the relationships for predicting the KPIs can be recalibrated. In particular, a trigger rule can be evaluated when new data is received. For example, a predicted value of a KPI can be compared to an actual value and when the difference is significant, such as beyond a threshold, recalibration can be triggered.

Recalibration can include adjusting parameters of a model based on new data. The system can also determine that the previous model no longer reflects the relationships between influencers and performance indicators. A model can be restructured to better reflect the relationships. In another example, a new influencer can be added to the model. In a further example, a new type of algorithm or model can be selected and the parameters determined for the new type of algorithm or model based on the new data and past data. Once recalibration is performed, the system can provide an updated prediction, root-cause analysis, or prescription.

Further, the system can provide a warning when suggested actions are not implemented. For example, when the system predicts that a future value of a key performance indicator will be in violation of a business rule and prescribes an action and when new data indicates that the action was not implemented and the key performance indicator will be in violation of the business rule, the system can provide an indication or send a message to a supervisor indicating that the actions were not taken. For example, an indication can be displayed on an interface device, sent via email, sent as a text message, or provided as a voicemail.

Such analytics and prescriptive methods can be implemented by analytics system. In particular, the analytics system may include one or more interfaces, one of which being a configuration script. The configuration script can be used to at least partially configure the analytics system in preparation for analysis and prescription processing.

Figure 9:
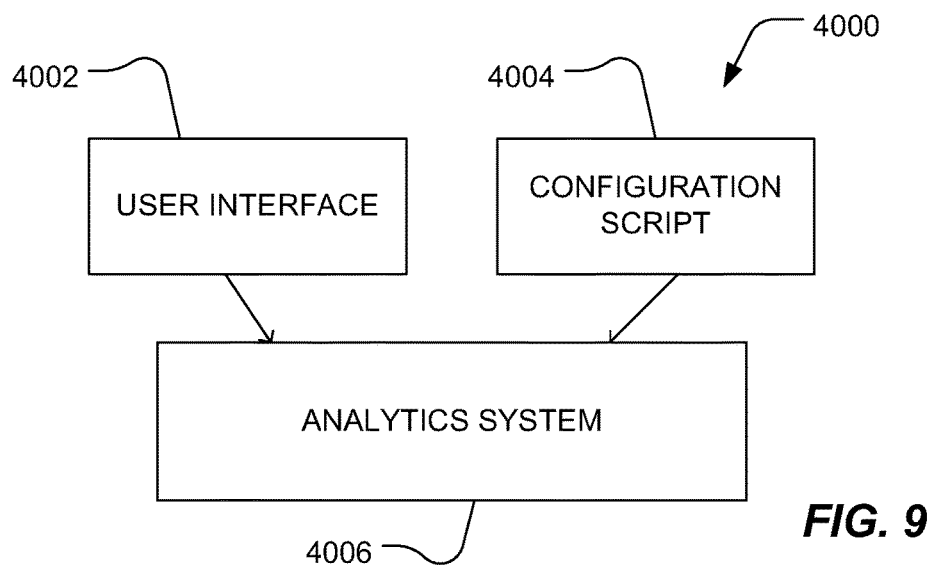
FIG. 9 includes an illustration of exemplary system including inputs into an analytic system.

For example, FIG. 9 illustrates a system 4000 that includes an analytics system 4006. The analytics system 4006 is in communication with a configuration script 4004. In addition, the analytics system 4006 may be in communication with a user interface 4002. Optionally, the user interface 4002 can be used to configure the analytics system 4006. The configuration script 4004 can be used to configure several subsystems of the analytics system 4006 with information relevant to each of the configured subsystems. In addition, the configuration script 4004 can include specific information to configure individual subsystems. For example, the configuration script 4004 can establish variables. Such variables can include influencers and performance indicators. Each of the subsystems of the analytics system 4006 can utilize the influencers and performance indicators as identified in the configuration script 4004 as part of their respective configurations. In another example, the configuration script 4004 can identify models and algorithms, as well as associated parameters, to be used by a particular subsystem of the analytics system 4006. Further, the configuration script 4004 can identify constraints, functors, thresholds, and other business criteria useful by one or more of the subsystems of the analytics system 4006.

In an example, an analytics system includes a preprocessing subsystem, an insight subsystem (also referred to as a modeling subsystem), a prediction subsystem, and a prescription subsystem. For example, as illustrated in FIG. 10, an analytics system 4100 includes a preprocessing subsystem 4102, an insight subsystem 4104, a prediction subsystem 4106, and a prescriptions subsystem 4108. A configuration script 4110 is accessible by each of the subsystems 4102, 4104, 4106, and 4108. In addition, each of the subsystems 4102, 4104, 4106, and 4108 can be accessed through a user interface, through which a user can directly enter parameters and select options. The user interface may also access the configuration script 4110 to populate the user interface.

The configuration script 4110 can identify a set of variables including influencers and performance indicators. The identified influencers can include immutable influencers and mutable influencers. Each of the subsystems 4102, 4104, 4106, and 4108 can utilize the identified variables to perform their respective function. In addition, the configuration script 4110 can identify algorithms, models, methods, or processes, as well as parameters, inputs and data useful by such algorithms, models, methods, or processes for a particular subsystem.

In an example, the analytics system 4100 includes a preprocessing subsystem 4102 which accesses raw data sources and formulates a data set useful by other subsystems of the analytics system 4100. For example, the preprocessing subsystem 4102 can access structured data sources 4112 and unstructured data sources 4114. Structured data sources 4112 can include databases, tables, spreadsheets, calendars, delimited data or structured text files. The processing subsystem 4102 can access such structured data sources 4112 and using specified algorithms and methods, parse, clean or otherwise restructure the data 4112 for use by other subsystems within the analytics system 4100.

Further, the preprocessing subsystem 4102 can access unstructured data sources 4114. For example, the unstructured data sources can include narrative text, audio, image or video. A selected unstructured data source can be processed through an interpreter 4116 to provide structured data in a form that other subsystems of the analytics system 4100 can use. For example, an interpreter may be used to sample narrative text from websites or user comments to evaluate user sentiment. In another example, a preprocessing subsystem 4102 can use an interpreter 4116 to determine sentiment based on audio files, such as audio files generated from customer service phone calls. In a further example, an interpreter 4116 can be used to process a video file to analyze human emotion relative to variety of subjects.

In an example, the interpreter 4116 defines a variable or entity, extracts the value of the variable and associates the value with a time. An exemplary interpreter for analyzing narrative texts can include word frequency counting, associating a word frequency value with the date of the narrative writing. In another example, an interpreter for video or photo images may identify a mouth or other facial feature and fit a polynomial to the facial feature, associating the parameters of fit polynomial with a time stamp of the video or photos. In another example, the time to be associated with the fitted polynomial parameters can be a file date, or the interpreter or user can identify a time of year based on the background within the video image or photo.

In order to process data, the preprocessing subsystem 4102 can access the configuration script 4110. The configuration script 4110 can identify variables for which data is to be processed. In particular, the configuration script 4110 can identify a variable, a data source associated with the variable, the type of data source, an algorithm, method, or interpreter to use in analyzing the data source, other parameters associated with the algorithm, method, or interpreter, a format of data to be provided to other subsystems within the analytics system 4100, or any combination thereof. For example, the configuration script 4110 may identify a structured data source 4112, a method to use with the structured data source, the type of data source to be processed, and a variable, such as an influencer or performance indicator, to associate with the data source. The preprocessing subsystem 4102 performs extraction, transfer, and loading (ETL) functionality, including cleaning, removing duplicates, normalizing data, and aggregating the data for use by other subsystems.

In another example, the configuration script 4110 can identify a data source such as an unstructured data source 4114, the nature the data source (e.g., narrative text, audio, image, or video), an interpreter 4116 to process the data source, and parameters associated with the interpreter 4116, as well as a variable to associated with the output from the interpreter.

An insight or modeling subsystem 4104 of the analytics system 4110 can utilize the processed data and formulate a model associating influencers with performance indicators. For example, the insight subsystem 4104 can access data provided by the preprocessing subsystem 4102. In addition, the insight subsystem 4104 can access the configuration script 4110. The configuration script 4110 can provide an identity of variables, such as influencers and performance indicators. In addition, the configuration script 4110 can identify which modeling technique to use in developing a model to associate influencers with performance indicators, as well as parameters associated with the selected modeling technique. For example, the insight subsystem 4104 can be configured to implement a model using a modeling technique such heuristics, regression models, Markov chains, time series models, state space models, Bayesian models, neural networks, or any other appropriate model, or any combination thereof. The configuration script 4110 can select a particular modeling technique to use with a set of data and parameters associated with the selected modeling technique. For example, a neural net modeling technique may be specified in the configuration script 4110 and a number of nodes or node levels to be used in developing a neural net model associated with the selected data. In a further example, the model type can be a genetic algorithm and parameters associated with such a genetic algorithm can include population size or a crossover operator. In an additional example, the model type may be a polynomial fit and the parameter may be an order of the polynomial. Additional parameters that may be associated with modeling can include selecting a training set size or tests set size and specifying how the training set is selected such as randomly or a specified set. In a further example, a k-fold training may be specified as a parameter to the model subsystem.

In another example, more than one model type and associated parameters can be specified in the configuration script, along with selection criteria for selecting a model. For example, several models of the specified model types can be derived from the influencer and indicator data. One of the models can be selected based on selection criteria, such as a measure of accuracy or error.

Once the model is developed by the insight subsystem 4104, predictions about the performance indicators can be made by the prediction subsystem 4106. In particular, the prediction subsystem 4106 may access the model developed by the insight subsystem 4104, as well as data formulated by the processing subsystem 4102. The prediction subsystem 4106 can project values of the associated variables including influencers, such as mutable or immutable influencers, and performance indicators based on a model developed by the insight subsystem 4104.

The prediction subsystem 4106 can also access the configuration script 4110. The configuration script 4110 identifies variables, including the influencers and the performance indicators. In addition, the configuration script 4110 can include parameters useful by the predictions subsystem 4106, such as a time horizon for making projections, time granularity associated with the steps towards the time horizon, and other features or parameters. In particular, the time granularity may identify an increment of time and may be stated in specific time increments, such as a week, a month, quarterly, annually, etc. Alternatively, the length of increment may be consistent throughout the system and the time granularity can be expressed as a number of increments (e.g., 1, 2, or 3). The time horizon can be established as an endpoint to the prediction to be provided to a user, such as in 3 weeks, in 4 months, three quarters from now, or 5 years from now. In particular, the time horizon can be expressed as a number of the granular periods (e.g., 1, 2, 5, or 10). The time granularity and time horizon are not limited by the above examples and can include time periods and increments larger or smaller than the above examples.

Utilizing the prediction system 4106, a prescription subsystem 4108 can provide a suggested course of action based on suggested influencer values at future time periods. For example, when a performance indicator is predicted by the predictions subsystem of 4106 to violate a business criterion or rule, the prescription subsystem 4108 manipulates the future influencer values to determine a pathway for bringing the performance indicator in compliance with a business criteria or business rules. The prescription subsystem 4108 can access the configuration script 4110 to utilize the identified variables, such as influencers and performance indicators. In particular, the configuration script 4110 can identify mutable influencers that may be manipulated by the prescription subsystem 4108 to bring the performance indicator in compliance with business rules or business criteria. Further, the configuration script 4110 can identify an objective function or performance indicator about which to optimize. The configuration script 4110 can also identify an optimization routine and associated parameters to be utilized by the prescription subsystem 4108 for finding a set of future influencer values that provide a desirable course of action to bring the performance indicator in compliance with business rules of business criteria.

The configuration script 4110 can further include business criteria, thresholds, rules, functors, and other elements to configure one or more subsystems, such as the predictions subsystem 4106 or the prescription subsystem 4108. For example, upon developing a prediction, the prediction subsystem 4106 can identify performance indicators that do not conform to business criteria or business rules. For example, the prediction subsystem 4106 can identify those performance indicators that cross a threshold. In another example, the configuration script 4110 can identify a functor placing limits on the rate of change of a particular mutable influencer. In cooperation with the prediction subsystem 4106, the prescription subsystem 4108 can formulate a desired set of future influencer values that conform to the limits placed on the influencer value by the functor identified by the configuration script 4110.

In particular example, such an analytics system 4100 can perform analysis of data and utilizing the configuration script, can process the data through each subsystem to provide a desirable set of user actions as indicated by the prescribed influencer future values. The user actions can be displayed on a display device.

In a further example, the configuration script 4110 can identify other configuration scripts to be incorporated into the configuration script 4110. As such, previously developed configuration scripts that provide a desired function or have been tested individually can be implemented in the configuration script 4110.

The functionality, such as data processing or extraction, transfer and load (ETL), modeling, prediction, or prescription is illustrated as being associated with a particular subsystem or module. Alternatively, the functionality can be split between subsystems or modules or two functions can be associated with the same subsystem or module. As used herein, separate logical modules providing, in combination, a function such as extraction transfer mode (ETL) are discussed a single module. Further, a logical module providing more than one of the above-described functionalities is treated as two separate subsystems or modules or a single logical module encompassing two functional modules or subsystems.

Figure 11:
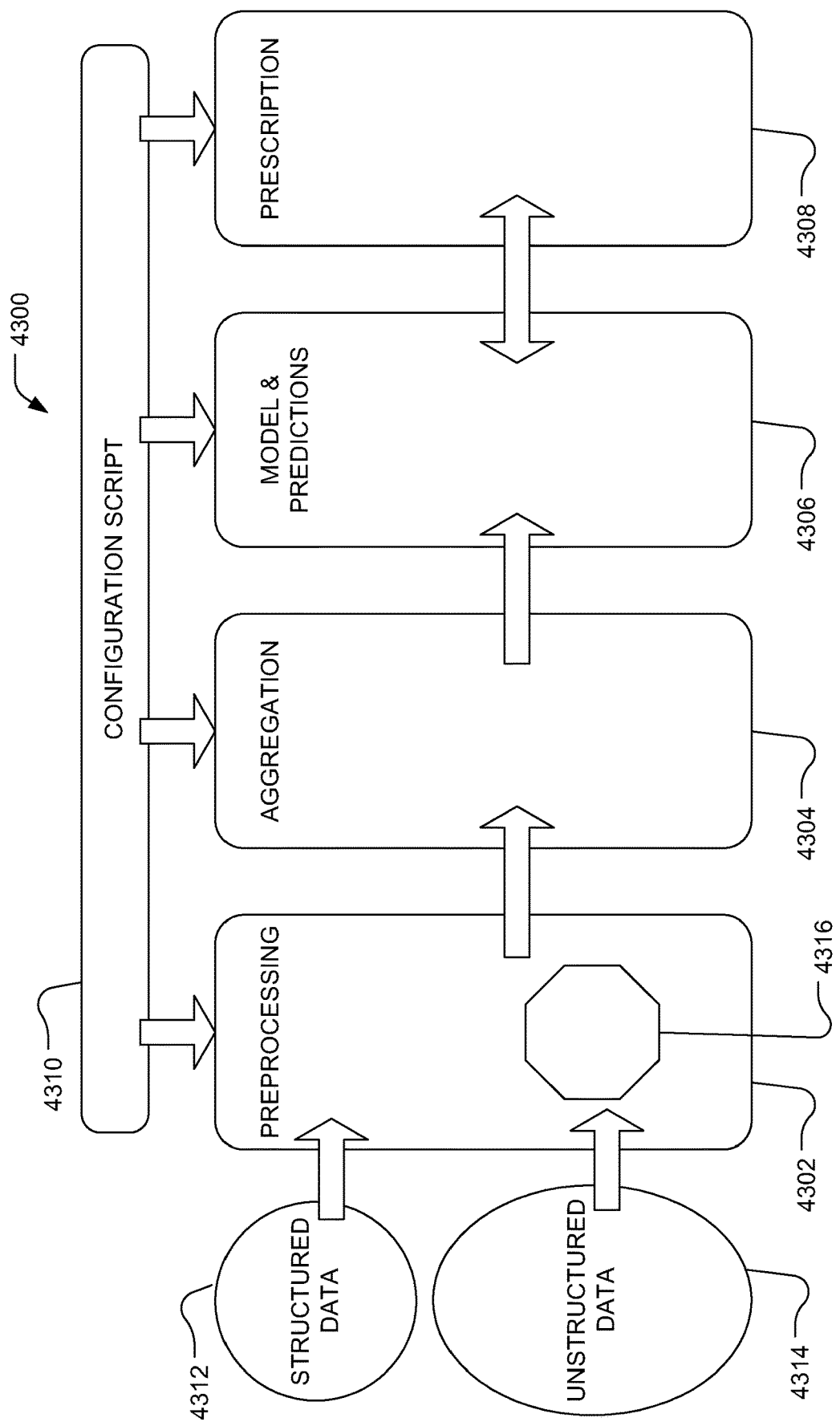

For example, FIG. 11 illustrates an analysis system 4300 including a processing subsystem 4302, an aggregation subsystem 4304, a modeling and predictions subsystem 4306, and a prescription subsystem 4308. A configuration script 4310 is in communication with each of the subsystems 4302, 4304, 4306, and 4308 of the analytics system 4300. In addition, each of the subsystems 4302, 4304, 4306, and 4308 can be accessed through a user interface, through which a user can directly enter parameters and select options. The user interface may also access the configuration script 4310 to populate the user interface.

As illustrated, the preprocessing subsystem 4302 accesses structured data 4312 and unstructured data 4314 and incorporates an interpreter 4316. The aggregation subsystem 4304 performs additional data processing functions, for example, aggregating data having a defined time granularity and determining derived variables based on expression. In combination, the preprocessing subsystem 4302 and the aggregation subsystem 4304 perform the extraction transfer load (ETL) functions useful for an analytic system 4300. As such, the preprocessing subsystem 4302 and the aggregation subsystem 4304 can be treated as a single subsystem or can be treated as two separate subsystem.

A model and predictions subsystem 4306 performs both modeling and prediction functionality and as such, can be a logical subsystem that incorporates two functional subsystem: one for modeling and one for predictions. In such an example, the model and predictions subsystem 4306 can access the configuration script to retrieve both scripting associated with modeling and scripting associated with predictions.

Figure 12:
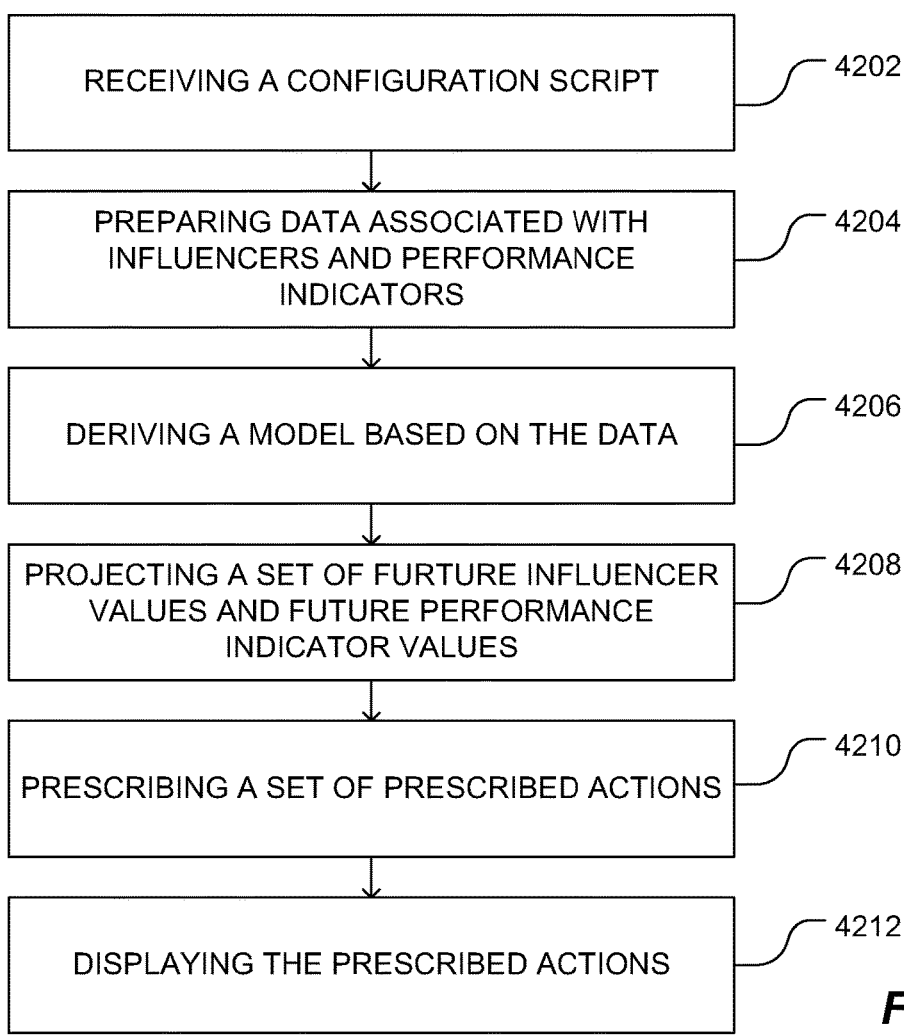
FIG. 12 includes a flow diagram illustrating an exemplary method for performing analytics, including prediction and prescription.

As illustrated in FIG. 12, an exemplary method 4200 includes receiving a configuration script 4202. The configuration script can identify elements useful by one or more of the subsystems of an analytic system. For example, the configuration script can identify variables, such as mutable influencers, immutable influencers, or performance indicators. Further, the configuration script 4202 can include identification of algorithms and associated parameters for use by each of the subsystems. For example, the configuration script can include identification of the data source, and the variable to be associated with the data source. In another example, the configuration script can include a selected model type as well as parameters to be used in developing a model of the selected model type. In another example, the configuration script can include a time horizon or time granularity to be applied to a prediction. In a further example, the configuration script can include an optimization algorithm or an objective function.

Based on information provided by the configuration script, data associated with influencers and performance indicators can be prepared, as illustrated at 4204. For example, a preprocessing subsystem can access a configuration script to determine a data source, the nature the data source, algorithms or interpreters to be utilized in accessing the data source, or which variable to associate with data acquired from the data source.

Utilizing the processed data, a model can be derived based on the data, for example, using an insight or modeling subsystem, as illustrated at 4206. In particular, the insight subsystem can access the configuration script to retrieve, identification of influencers and performance indicators, a model type and parameters associated with formulating or developing a model of the selected model type. The insight subsystem can derive the model utilizing the information of the configuration script.

As illustrated at 4208, a set of future influencer values and future performance indicator values can be projected, for example, by a prediction subsystem. The prediction subsystem can access a configuration script to identify influencers and performance indicators. In addition, the predictions subsystem can access the configuration script to retrieve a time horizon and time granularity to be associated with the projected future influencer values and future performance indicator values.

As illustrated at 4210, a set of prescribed actions can be prescribed, for example, by a prescription subsystem. The prescription subsystem can access a configuration script to identify mutable influencers, as well as performance indicators. In addition, the prescription subsystem may access the configuration script to identify an objective function, optimization method, and parameters associated with the optimization method. Further, the prescription module may access the predictions subsystem and iteratively perform predictions based on the prescribed future influencer values.

Once a set of prescribed future influencer values is determined, the prescribed influencer values may be translated into prescribed actions and displayed, as illustrated at 4212. For example, the future influencer values may directly identify user actions to be implemented to maintain the performance indicators in compliance at a future date. Alternatively, the influencer values may be translated through an algorithm into select user actions that can be implemented by a business. Such user actions can be displayed, as illustrated 4212.

In an embodiment, the configuration script can take the form of a domain-specific language (DSL). In an example, the script can be a program. In the example below, the configuration script shares similarity with programming languages, such as C++. However, a configuration scripting syntax can be configured to emulate the syntax of other programming languages or follow a unique syntax.

In an example, the configuration script identifies variables for use by the analytics system. For example, the configuration script can identify variables, such as mutable influencers. In another example, the configuration script can identify immutable influencers, mutable influencers, performance indicators, or a combination thereof. The configuration script can include a section marker, for example, identified with a leading "#" marker. For example, a mutable variable ("material") may be identified as:

mutables
material;

Where the influencer is constrained, such as with a set limit or with a functor, the influencer may be characterized by the constraint.

mutables
engineering_staff=m*t+b
m>=−1
m<=10
b>=1;
engineering_hours<=1000;

A variable can be a continuous variable, an integer variable, or a categorical variable, among others. As such, a constraint associated with the variable can be expressed in a manner consistent with the variable's nature. In particular, a constraint section can define constraints or business rules associated with variables other than mutable influencers.

//identifies the constrain section
constraints
// a continuous variable with a constraint
burn_rate<=1000;
// a categorical variable, where !@ is NOT IN
shipping !@ {truck, train};

Such constraints can include functor constraints (constraint functions of time or other variables) having a linear or higher order expression in terms of time or optionally in terms of other variables. As such, a constraint relationship between a variable and time or between two variables can be established. For example, three variables may be constrained so that their sum cannot exceed a fixed value. Further, the constraint section or a separate business rules section may identify thresholds or other boundaries that if crossed by a performance indicator indicate a problem, error, or undesirable condition.

The configuration script can further include sections specific to subsystems within the analytics system, for example, identifying algorithms to be used by the subsystem and specifying parameters associated with the algorithm. In an example, the configuration script can identify a data source, an associated algorithm for processing the data source and the variable to associate with the data source. The data source can be structured or unstructured.

//identifies a data section
data
//identifies a structured data source, associated variable, and parsing method
data_source_1="\\data_folder\data_file.txt"
engineering_staff
tab_delimited;
//identifies an unstructured data source, associated variable, associated type, interpretation method, and a parameter associated with the interpretation method
data_source_2="\\data_folder\interview.mp3"
customer_sentiment
audio_mp3
sentiment_module_2
p=3;

In another example, the configuration script can identify a model for use by a modeling subsystem or an insight subsystem. For example, the configuration script can include a model section and specify a model algorithm and associated parameters.

//identifies the model section
model
//identifies the model and associated parameters
nueral_net_module_2
level=3

More than one model can be identified. In addition, selection criteria can be identified for selecting between models for the system or for a particular performance indicator. Exemplary selection criterion can include accuracy or error rates, deviations, $R^2$ factors, or other criterion.

In a further example, the configuration script can specify parameters for a prediction, such as a time horizon or a time granularity. The time granularity can specify a period (e.g., days, weeks, months) or if the period is consistent throughout the system, can specify a number of periods (e.g., 1, 2, and 5). The time horizon can specify the last period (e.g., 5 for the fifth period). Alternatively, the time horizon can specify a specific time. For example, the configuration script can provide a predictions section.

```
//identifies the prediction section
#prediction
//identifies a time granularity
granularity=weeks;
//identified a time horizon
# at
5; // Weeks #5 (from "now").
```

In a further example, the configuration script can provide a section for prescriptions. The prescriptions section can identify an optimization routine, a performance indicator around which to optimize or an objective function, or a time horizon or endpoint.

```
//identifies a prescriptions section
#prescription
//identifies a performance indicator around which to optimize
profit;
#at
5; // Week #5 (from "now").
```

When a time horizon is specified for both the predictions subsystem and prescriptions subsystem, the time horizon specified for the prescriptions subsystem can take precedent during the prescriptions operation. Alternatively, the time horizon specified for the predictions subsystem can take precedent.

In an additional example, the configuration script can incorporate other configuration scripts. For example, previously developed scripts can be incorporated to simplify operations and reuse established scripts.

```
//file inclusions
#include "other_script.pal"
```

The analytics system can further include a parser to assist with subsystem access to the items of the configuration script. In an example, the parser can construct objects accessible to the various subsystems.

The analytics system, associated subsystems, configuration script, parser, and data sources can be implemented on one or more computational devices connected through various communications protocols. In particular, access between a subsystem and another subsystem can be facilitated by direct communication or by communication through data storage accessible to both subsystems. Similarly, access from a subsystem to the configuration script can be facilitated by direct access to the script or to data objected parsed from the configuration script.

Figure 13:
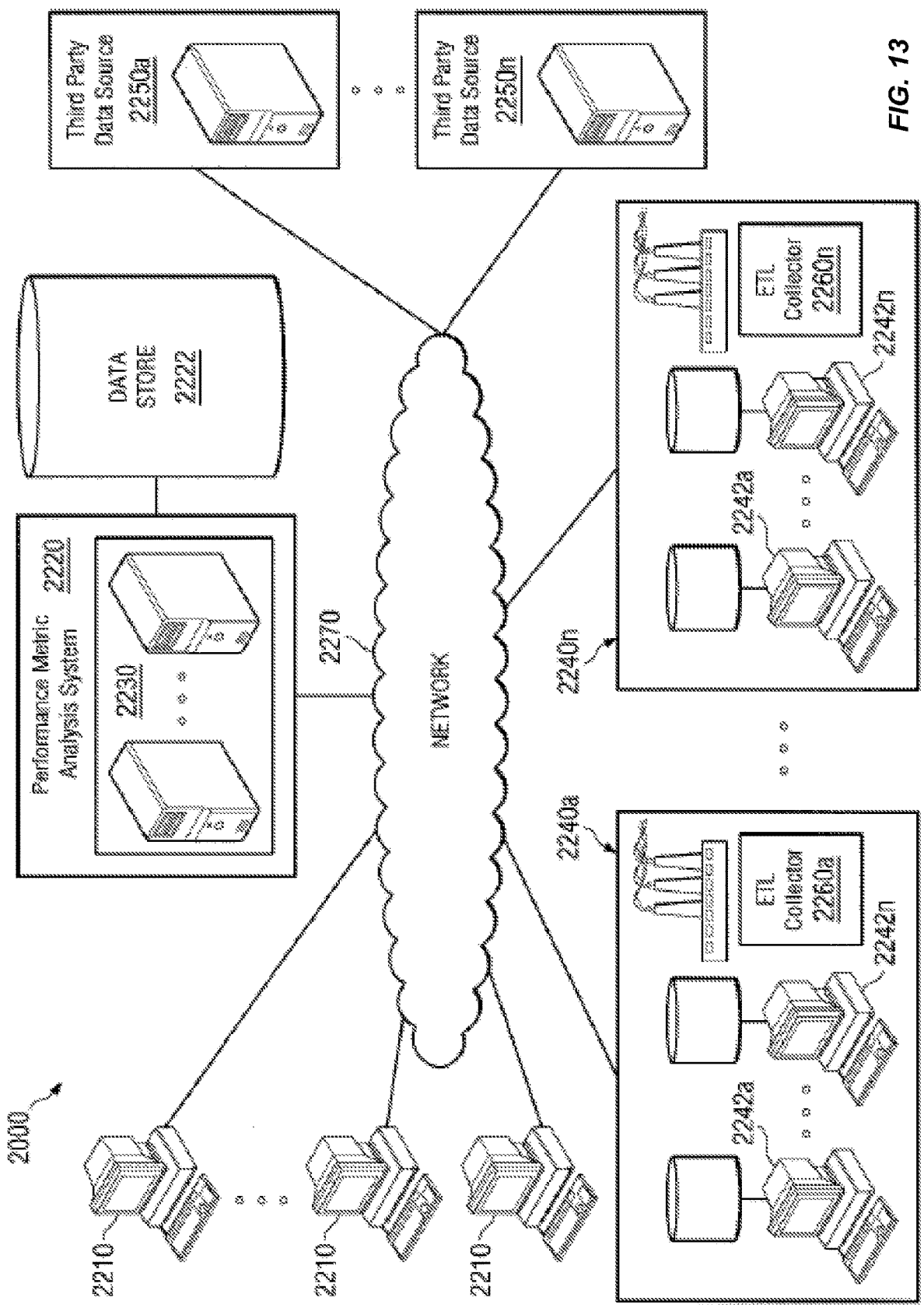
FIG. 13 is a block diagram illustrating an embodiment of a topology that can be used in conjunction with an implementation of embodiments of the present invention.

While a variety of system topologies can be used to implement the above described system, a topology, such as the topology illustrated in FIG. 13 can be used to implement embodiments of the systems and methods. Topology 2000 comprises performance metric analysis system 2220 (including associated data store 2222) comprising one or more computer devices 2230. These computing devices 2230 can, for example, by organized as a cluster which can be a loosely or a tightly coupled cluster and include one or more load balancers (not shown). Performance metric analysis system 2220 (e.g. one or more of computing devices 2230) can be coupled through network 2270 to computing devices 2210 (e.g. computer systems, personal data assistants, kiosks, dedicated terminals, etc.), one or more locations of an entity 2240 and one or more third party data sources 2250 operable to provide, for example, market data, benchmarking data, etc. Network 2270 can be for example, the Internet, a wide area network (WAN), a local area network (LAN) or any other type of conventional or non-electronic communication link such as mail, courier services or the like.

Generally speaking then, entity 2240 can be a business, non-profit, or other type of entity which implements a process. This process can, for example, be a business process which relates to the functionality or performance of the entity. As discussed above, for example, such business processes can comprise the implementation of customer service through a contact or call center, the implementation of transaction services, the management of supply or demand chains or other inventory management, the implementation of field services, the implementation and management of sales pipelines, etc.

No matter the type of processes implemented by the entity 2240 however, it can be useful to measure or otherwise analyze (including predicting, simulating, optimizing, etc.) the performance of such a process utilizing a performance metric, such as a KPI as discussed above. Accordingly, entity 2240 can desire to utilize and monitor these performance metrics related to these processes for a variety of reasons, including improving the performance of such processes, reducing the cost of implementing such processes, controlling the quality of such processes, preempting issues which can occur in the future with respect to these processes, substantially optimizing solutions to future problems and predicatively determine the effect of certain solutions to anticipated future problems, etc.

To that end, performance metric analysis system 2220 can gather data from entity 2240 or a third party data source 2250 to analyze such data to perform analysis on such data and can present an interface such that one or more users at computing devices 2210 can determine what analytics are utilized, the data used for these analytics, view, or affect the results, of such analytics, etc. Embodiments of such interfaces have been discussed previously herein.

More specifically, in one embodiment, performance metric analysis system 2220 can implement a set of analytics comprising at least predictive analytics, root-cause analytics, optimization and what-if simulation. Colloquially speaking, predictive analytics allows users (for example, associated with entity 2240) to identify and quantify problems (including opportunities) related to one or more performance metrics, root-cause analysis allows users to identify, quantify and rank influencers of performance metrics which can cause any upcoming problems, optimization can determine substantially optimum solution to preempt (or benefit from) any determined upcoming problems and what-if simulation allows a user to determine the effect of prescribed solutions on performance metrics.

To implement such analytics, performance metric analysis system 2220 can gather data directly or indirectly related to one or more performance metrics from entity 2240. Entity 2240 can have multiple locations 2240a, 2240n where each entity location 2240a, 2240n can comprise multiple servers or other types of computing devices 2242 which are involved in the implementation of the process by the entity 2240 or the storage of data involved with the implementation of the process. In some instances, entity locations 2240a, 2240n can have computing devices which run according to different operating systems or protocols, or which implement different types of applications or databases in conjunction with the process.

Each entity location 2240a, 2240n can have an associated ETL collector 2260 which is responsible for collecting appropriate data regarding the process or one or more associated performance metrics from various computing devices 2242 utilized in the implementation of the process or used to store data involved with the implementation of the process. ETL collector 2260 can send the data gathered at the corresponding entity location 2240 to the performance metric analysis system 2220 in response to a request from the performance metric analysis system 2220.

Thus, performance metric analysis system 2220 can, based upon one or more schedules, send out requests to each ETL collectors 2260 at each of the entity locations 2240a, 2240n and receive, in response, a set of data corresponding to that performance metric and that entity location 2240a, 2240n collected over a certain time period. This data can be stored in data store 2222. Analytics can then be performed by the performance metric analysis system 2220 using the data gathered from the entity locations 2240a, 2240n. The analytics performed by performance metric analysis system 2220 can be determined, at least in part, by a user's interaction with an interface presented by performance metric analysis system 2220 and the results of the analytic performed can similarly be displayed to a user through the provided interface.

Not all of the various entities depicted in topology 2000 are necessary, or even desired, in embodiments, and that certain of the functionality described with respect to the entities depicted in topology 2000 can be combined into a single entity or eliminated altogether. The topology 2000 is therefore exemplary only and should in no way be taken as imposing any limitations on embodiments herein.

Each of the above disclosed methods can be performed on multiple systems. For example, the methods can include processing data streams from a file system. The file system can be distributed, particularly for large data sets. A method can be partitioned in such a way, that it can perform the operations on a partition or subset of the data. Such processing is particularly useful for unstructured data sources having large file size. The results of such processes can be combined in such a way that the result is identical to the method applied to a single data source being combined of all of the partitioned data.

In different embodiments, any presently-disclosed apparatus (or any presently disclosed computer product including a computer usable medium) can be configured or operative to any presently disclosed method or technique.

A computer program product, includes a computer usable medium having a computer readable program code non-transitorily embodied therein, said computer readable program code adapted to be executed to implement a method as described above. Computational subsystems can be implemented on the same computer or implemented as separate computers. The terms "module" and "subsystem" are used interchangeably herein.

In the present disclosure, certain routines for calculating data or displaying data may be carried out 'in accordance with' a certain factor—for example, influencer identifiers may be ordered or selected in accordance with magnitudes of one or more deviations. When a routine is carried out 'in accordance with' a certain factor or factors, the routine can also be carried out in accordance with one or more 'additional factors' or additional business rules (for example, displayed identifiers may be ordered both according to magnitudes of deviations as well as whether or not the influencer is designated as an 'external influencer' or a 'controllable influencer.'). In the present disclosure, the phrase 'in accordance with' (or 'according to') should be interpreted as 'at least in part in accordance with.'

As described above, "controllable influencers," "actionable influencers," and "mutable influencers" are analogous terms. In an example, an influencer can be a business input. For example, an influencer can be a measurable business input, such as a business input relating to an action, a business function, or other business relevant data. A key performance indicator can be a business output, such as a measurable indication of performance of a business function.

In a particular example, the system can be used for resource production. Exemplary resource production can include asset production from land based resources or other constrained resources. For example, resource production can extend to mining, drilling, and agriculture, among others. In a particular example, the resource production include oil production.

In oil production, with the value of the end product determined by global commodity economics, the basis of competition for operators in upstream exploration and production is the ability to effectively deploy capital to locate and extract resources more efficiently, effectively, predictably, and safely.

In unconventional resource plays, operational efficiency and effectiveness is diminished by reservoir inconsistencies, and decision-making impaired by high degrees of uncertainty. These challenges manifest themselves in the form of low recovery factors and wide performance variations.

Conventional techniques relying on modeling, assumptions, and estimations have proven inadequate in highly complex unconventional resource plays, and legacy analytic tools and technologies have been unable to keep pace with the explosion of data generated and captured by producers and their ecosystem of service providers.

The proposed system helps operators anticipate and improve wells. The proposed system incorporates data, regardless of source, structure, size, or format, to prescribe actionable recipes for drilling, completing, and producing wells that maximize their economic value at every point over the course of their serviceable lifetimes. The bottom line for operators is improved returns on deployed capital: more oil, more predictably, for less cost.

As exploration and production companies transition from securing acreage to producing it, efficiency and effectiveness matters more than gross production volume. Markets reward producers that are not simply able to produce more hydrocarbons, but recover them cheaper, faster, and more consistently. Avoiding the superfluous or suboptimal deployment of capital is particularly important to smaller independent producers, as maintaining adequate borrowing capacity is existential. The significance of operational efficiency and effectiveness intensifies in volatile or deflating price environments.

Operators face challenges including 1) establishing the repeatable, scalable processes to improve the value of the operators' asset portfolio; 2) decision-making is impaired by reservoir inconsistencies, variability, and high degrees of uncertainty; 3) variability: shale plays are notoriously inconsistent, with a large number of widely variable engineering parameters and geologic properties; 4) complexity: (The interrelationships between and among controllable and uncontrollable variables that influence production and drive well-scale economics are often unclear or unknown. As such, it is difficult to diagnose cause and effect with confidence); 5) uncertainty: values or ranges for a number of critical variables and reservoir parameters are often unknown; and 6) technological limitations and constraints: (Oil and gas producers and their ecosystem of service providers are producing and capturing more data than ever before). These complex, varied, and massive data sets are being generated at an ever-increasing velocity. Any one of these factors—volume, variety, or velocity—can overwhelm the capacity of legacy tools and technologies, to say nothing of all three at once.

Technological and analytical limitations and constraints often lead to operators oversimplifying complex problems. While widespread adoption of models, assumptions, and estimations may have been adequate for conventional reservoirs, this approach has proven inadequate in highly complex unconventional resource plays.

The operator's business problems and their root causes manifest themselves in the following ways:

Planning
Reliance on a "manufacturing" approach to improve asset economics;
Inability to correlate cause and effect with accuracy and confidence;
Standardized well designs;
Overreliance on inference, assumptions, and models;
Execution
A trial-and-error approach to incremental improvement;
Geometric completions;
Inability to accurately measure completion effectiveness;
Results
Low recovery factors;
Wide performance variations.

Unable to optimize on a per-well basis, operators look to influence economic returns through cost and process efficiencies, shifting the focus from making money to saving money. However, such approaches are often suboptimal.

The proposed system incorporates data, having a variety of sources, structures, sizes, or formats, to prescribe recipes for drilling, completing, and producing wells that improve economic value over the course of their serviceable lifetimes. The proposed system provides recipes that incorporate location-based physical and geologic characteristics, as well as constraints and objectives and operator-specific asset management strategies.

The end result is compressed learning curves and an improved return on deployed capital: more oil, more predictably, at a lower cost than what is occurring today. For example, results can include increased recovery factors, faster breakeven/payback, higher rate of return, higher asset net present value, accelerated development of the highest return assets, reduced surface footprint, and elimination of marginal or uneconomic wells.

In particular, the proposed system can provide for analysis of field data on an on-going basis. The limitation of traditional analytic tools and methodologies has been an inability to incorporate the breadth of data that generates meaningful results. Legacy analytic tools are simply incapable of incorporating unstructured data—video, images, acoustics, free texts, and such—into their algorithms.

The proposed system incorporates data from many source, in formats—including audio, video, image, text, and numbers—in order to extract insights and generate dynamic prescriptions for more efficient, effective, repeatable, and scalable production.

In particular, the proposed system integrates the data and continually analyzes it together to generate actionable recommendations for changes that produce better results.

Further, the proposed system predicts, prescribes, and adapts. The system generates predictions and prescriptions using a number of analytic techniques and scientific disciplines in combination, including adaptive machine learning, meta-heuristics, operations research, and applied statistics, operating within the context of client-defined business rules.

As a result, the system is able to predict future outcomes and generate actionable recommendations to benefit from the predictions. Because real-world conditions are anything but static—especially true in shale plays—the system can continually incorporate new data to re-predict and re-prescribe, thus automatically improving prediction accuracy and prescribing better decision options.

Figure 14:
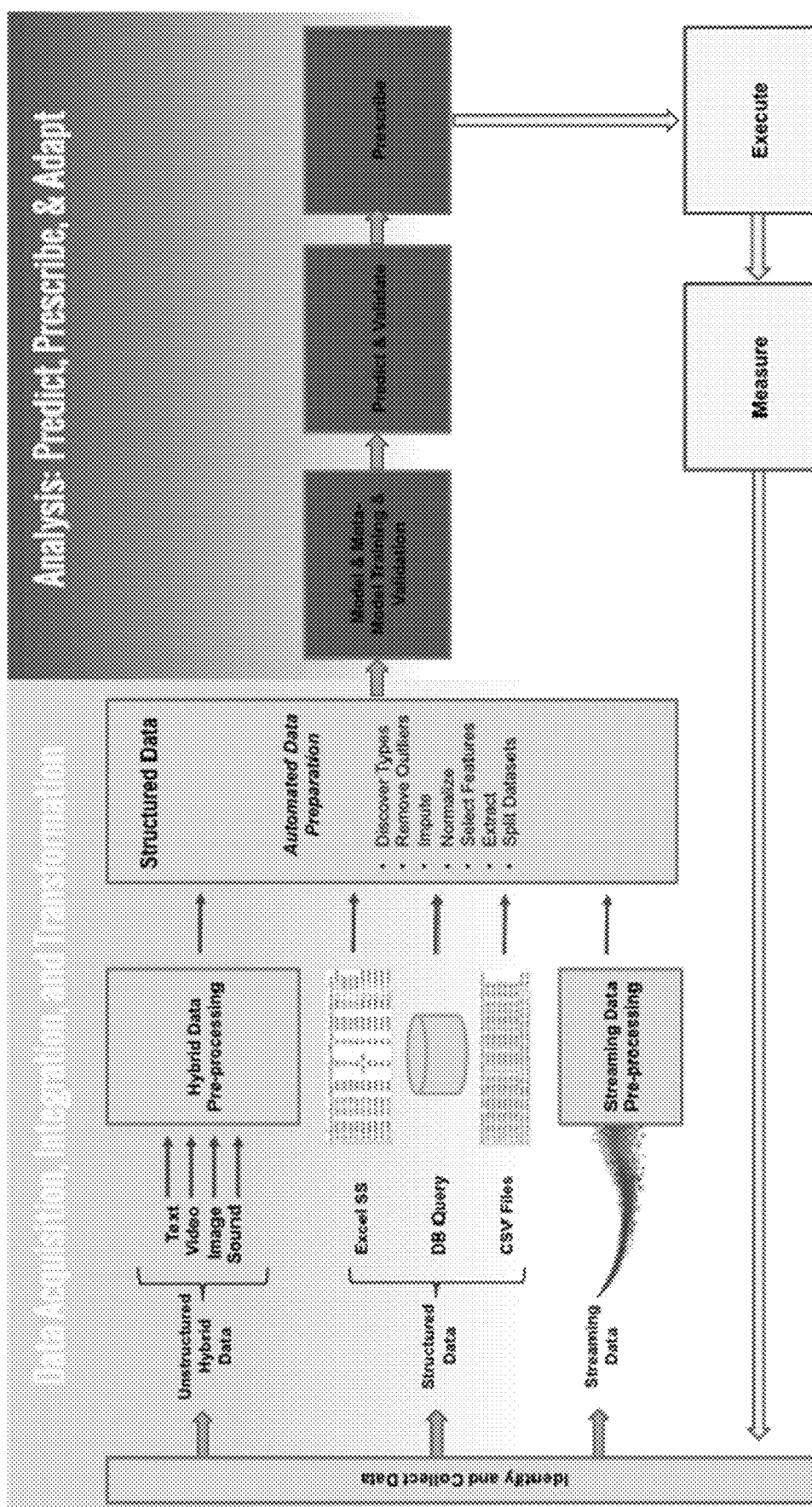
FIG. 14 and FIG. 15 include flow diagrams illustrating exemplary processes.

As illustrated in FIG. 14, the system can identify and collect data. The data can include unstructured/hybrid data, structured data, or streaming data. Exemplary unstructured/hybrid data includes text video, images, and sound. Structure data can include spreadsheets, database queries, and other structured files, such as CSV files. Streaming data can include structured or unstructured data that arrives periodically in a data stream. As used herein, structured data has a pairing of at least two data values, whereas unstructured data lacks such a pairing.

The unstructured data can be preprocessed and the streaming data can be preprocessed to form structured data useful in the analysis process. The system can further prepare the structured data by discovering types of data, removing outliers, imputing missing data, normalizing the data, selecting features, extracting, and splitting data sets. The structure data can be used in modeling and meta model training and validation. Resulting models can be used to predict and validate performance of the process being modeled and to prescribe new actions that can be executed, measured and provided to the system.

In a particular example, the unstructured data can include drilling reports, which are narrative text reports that typically incorporate notes by an operator utilizing various acronyms, lingo, and depth information. Often, the drilling reports include multiple acronyms that refer to the same factor. In a particular example, the drilling reports can be applied to a model developed with machine learning to ascertain important events and the associated depth at which those events happen. Such events and their associated depth can be fed through the structured data to the modeling training and validation and be used for prediction and prescription. The machine learned model can include a neural network, a classification model, or a combination thereof. In an example, the classification model can be a heuristic classification model. In another example, the model can include convolutional neural networks, recurrent neural networks, or any combination thereof.

In a particular example, the data is prepared by feature selection, data type conversion, record selection, outlier removal, and missing value imputation. For example, feature selection can include removing identification figures, removing underrepresented features, removing low or zero-variance features, and removing highly correlated features (e.g., having a correlation coefficient of at least 0.5). Data type conversion can include converting categorical string data into numerical data. In another example, record selection can include removing data associated with wells missing a target value (e.g., 180-day cumulative production). Outlier removal can include removing values having 5 standard deviations from a feature mean.

In an example, missing value imputation can include preparing a model to impute production values for days when production is influenced by something other than well performance, such as upstream maintenance issues, shut-ins, weather related issues, among others. In an example, production data is reviewed for the first window during which the well produced for a majority of the time. For example, the window can be a 30-day window, but other window durations can also be envisioned. In such an example, the production data can be reviewed for the first 30-day window in which there are 20 days of production. For days of no or little production, values can be imputed using production values from a combination of days before and after. In a particular example, the production can be imputed from an average of actual production values from 3 days before and 3 days after the no or low productions day. The process can be continued for periods extending beyond the window, such as to 60 days, 90 days, or 180 days, for example.

Figure 15:
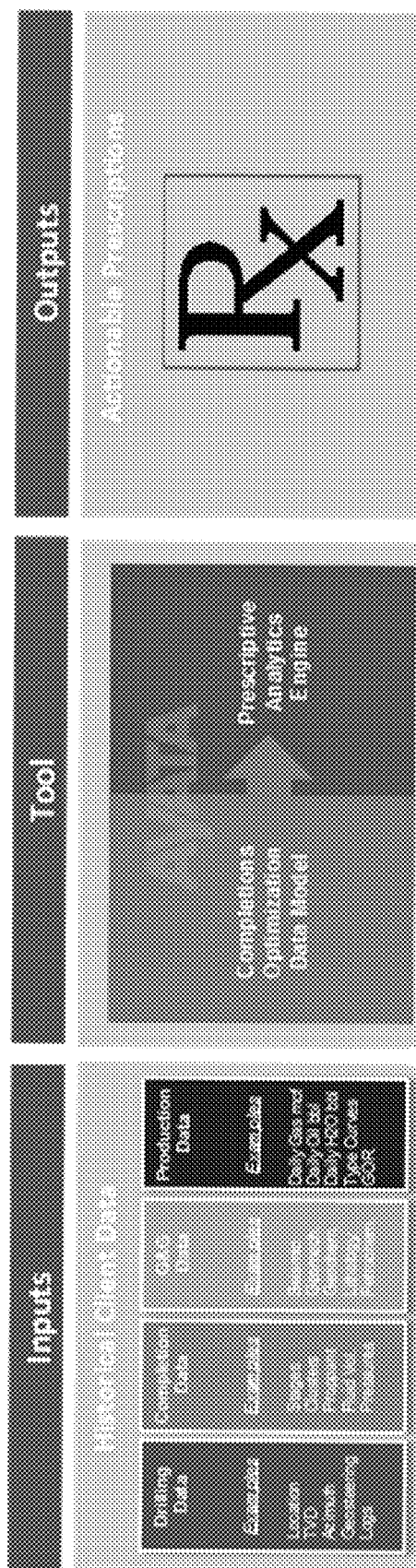

As illustrated in FIG. 15, historical data, such as drilling data, completion data, geological and geophysical data, and production data, can be utilized to form a field specific model. As used herein, a field specific model is a model derived from the data, but is not a finite element or finite difference model. Exemplary drilling data can include surface location, total vertical depth (TVD), azimuth, dip, inclination, geo-steering, logs, and drilling reports. Exemplary completion data can include completion date, treated lateral length, number of stages, treated length per stage, clusters (number and spacing), perforation density and phasing, proppant type and amounts, fluid type and volume, and treating pressures, rates and duration, or initial or final frac gradients associated with completion and treatment of the wells. Exemplary geological and geophysical data can include stress or pressure gradients, raw or composite geologic attributes (such as Mu, Rho, Lambda, Mu*Rho, or Lambda*Rho), Eta, coherency, curvatures, delta T, DTSM, or mineralogy (volumetrics by weight or percentage), among others. The data can also include seismic, geomechanical, geochemical, lithology, or petrophysical or petrochemical data. Exemplary petrophysical data can include gamma ray log data, porosities (raw or adjusted), permeability, saturations (oil, gas or water), resistivity, or density. Exemplary reservoir data can include thickness, TOC, OIP, or GIP. Exemplary geochemical data can include Young's modulus, Poisson's Ratio, closure stresses, or XRF. Exemplary production data can include date of first production, a number of days of oil/gas/water production volumes (e.g., 30 days, 90 days, or 180 days), daily gas output, daily oil output, daily water output, type curves, fluid properties, or GOR.

Such data can be used to further create synthetic variable data. A synthetic variable is derived from one or more other variable. A synthetic variable can be an algebraic combination of variables, a step function, or a combination thereof. In a particular example, the synthetic variable is derived from a time factor in addition to other factors. For example, a synthetic variable referred to as a proximity depletion variable can be determined based on Euclidean distance between stages of nearby wells, a time difference between completion, and a depletion curve. In particular, the proximity depletion variable can include a step function in either time or distance and be proportional to time, distance, production, or a product, quotient, sum or difference thereof. In another example, a fracking order feature variable can be determined based on fracking end dates of wells proximal to each other and having parallel laterals. In a further example, a synthetic variable can include a fraction hit feature, which quantifies the effect of completing a new infill well in the vicinity of producing wells. In an additional example, a synthetic variable can include a flow feature, which separates the impact of operational policies, such as shut-ins and choke restrictions, to isolate the impact of completion design decisions on production.

Such data can be utilized to create a drilling engine, a completions engine, a production engine, or a combination thereof. In an example, the system can include a plurality of engines, such as a plurality of completion engines. Each completion engine, for example, can be associated with a different geological structure. In another example, each completions engine can be associated with a different formation type. The engines are derived from field specific models associated with a specific basin, reservoir, geological structure or formation. The different engines can include neural networks, regressions, classifications, or other engine types, or a combination thereof.

The completions engine can derive completions parameters from an associated set of variables. The variables include given variables and actionable variables. In an example, the actionable variables can be ranked by influence on the completions parameters. The set of variables can include synthetic variables. For example, the set of variables can include a proximity depletion synthetic variable.

In an example, the completions engine is derived based on machine learning using a machine learning technique. Such as machine learning technique can be automatically selected by the system from a set of machine learning techniques, such as random forest, linear regression, stochastic gradient descent, K-neighbors, Bayesian ridges, or combinations thereof. The completions engine can incorporate a neural network or a regression based on correlations derived from a field specific model.

The system can include two or more completions models, e.g. for different fields. Each completions model has an associated set of variables. The associated set of variable can include different variables than sets of variables associated with other completions models. In another example, the associated set of variables can be ranked differently than the rankings of variables associated with other completions models.

The system can also include drilling engines, production engines, or analysis engines incorporating structures associated with neural networks, regressions, and classifications.

The prescription analytics engine can utilize the engines to prescribed actions taken by an operator or driller, or field management. For example, the prescription analytics engine for a particular well can prescribed a treated lateral length, number of stages, proppant quantity, proppant concentration, a proppant mix, the amount of proppant per gallon, a flow rate of proppant, or a combination thereof, among others.

Further, the prescription analytics engine can include financial projections and optimization can be performed based on a financial projection constraint. For example, design, completion, or operations parameters can be prescribed to provide a desirably high net present value of the well. In another example, design, completion, or operations parameters and operational parameters can be provided to provide high total output. In an additional example, design, completion, or operational parameters can be provided for a well having a constraint completion cost, improving the net present value given the completion cost constraint. In other examples, the prescription analytics can further incorporate financials for a field reservoir as a whole, providing for a number of wells, the speed at which new wells are drilled, optimizing for total output field or individual well production, and total net present value of the reservoir.

Figure 16:
FIG. 16 includes an illustration of an exemplary interface.

The output of the prescription can be displayed to the user, for example, as illustrated in FIG. 16. In particular, the output can display design, completion, and operational parameters as a list of actionable variables. The list can be an ordered list. For example, the list can include an order or higher influence variable to lower influence variables. The system can provide both a current value of the actual variable and a proposed improved value. Optionally, the display can further display reservoir parameters.

In addition, the system can display the projected production forecasts based on the present parameters and the improved values, as well as financial projections based on the current values and the improved values. As such, the system can provide both projected production values based on the prescribed values and current values, as well as the financial projections such as the present value, rate of return, and payback period.

In a further example, the system can associate wells drilled within the field to determine the influence of a given well on other wells, assist with predicting the performance of the well given its associated wells, and further predict field performance based on the behavior of wells within the system and the influence of wells on other associated wells. For example, FIG. 17 illustrates a set of wells 1702. The system can selectively associate (1704) wells to synthesize features and variables that influence field production and individual well production.

Further, the system can prescribe subsequent wells and predict the influence of such wells on future production of adjacent wells and the field as a whole. For example, as illustrated in FIG. 18, the field 1800 can include wells 1804. The prescribed well 1802 can influence the production of other wells 1804. The system can project production and financial consequences for the individual wells and the field as a whole.

As illustrated in FIG. 19, the system can further utilize operational parameters and drilling and completion parameters to predict production and prescribed operational parameters to enhance the desired output or net present value. For example, as illustrated in FIG. 19, t0 represents the beginning of production. The time prior to the beginning of production represents the design and completion of the well. In an example, the operator can utilize the design and completion data to predict operational parameters that will influence production through first 30, 90 or 180 days or beyond or for the lifetime of the well. In addition, the operator can utilize data from the design and completion of the well, as well as production through a first period, such as 30 days, to prescribe operational parameters for the well going forward. In addition, the system can provide guidance as to how the operational parameters implemented in the first 30 days affect production through the first 90, 180 days or the lifetime of the well. Such prescriptions can also indicate when artificial lift is to be installed and other such treatments. Another exemplary prescription includes enhanced recovery options.

Figure 20:
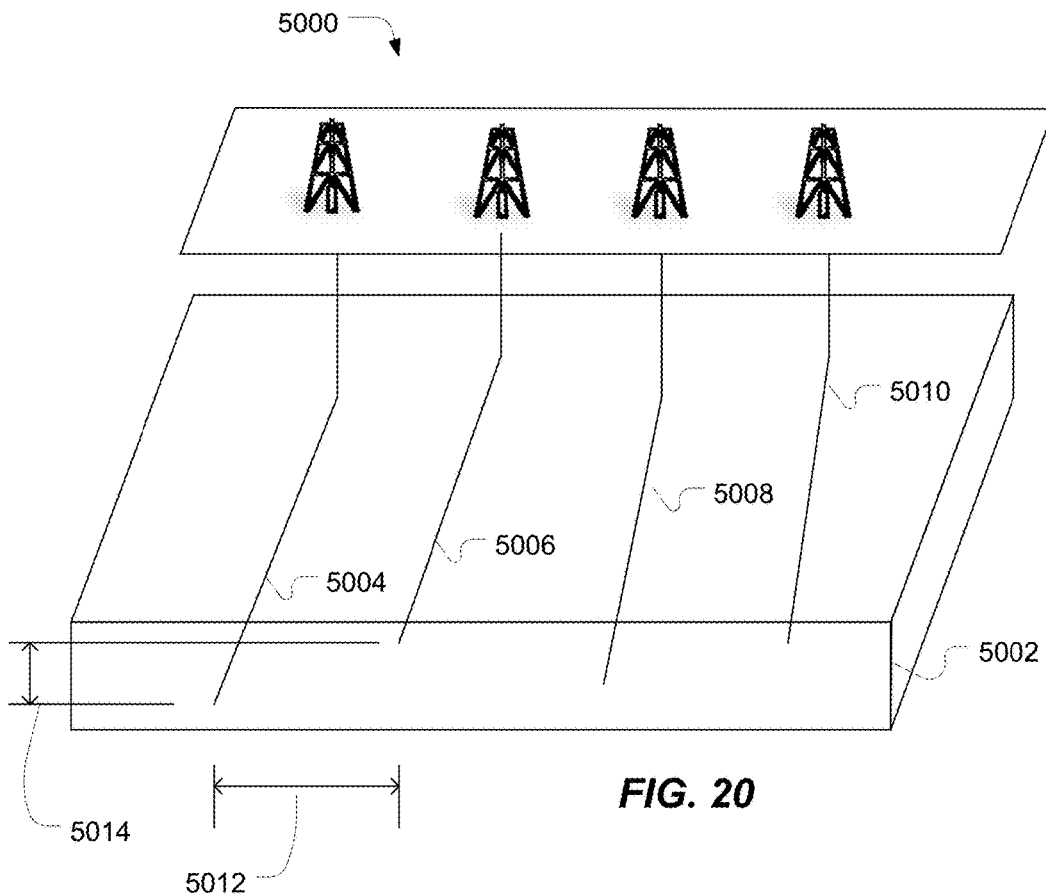
FIG. 20 includes an illustration of wells.

As illustrated in FIG. 20, set of wells 5000 can include runs that extends through a producing structure 5002. As illustrated, the horizontal portions of the wells 5004, 5006, 5008, and 5010 extend approximately parallel to each other through the structure 5002. But, the producing runs of each of the wells 5004, 5006, 5008, and 5010 can reside at a different height within the structure and run at slightly different angles providing different horizontal distances between wells. For example, the horizontal portion of the well 5006 can extend through the structure 5002 at a vertical position higher than the horizontal portion of the well 5004, as indicated at 5014. In addition, the wells 5004 and 5006 can extend with an average horizontal distance 5012. It has been found that several factors influence the production and depletion curves of the individual wells, including proximity to adjacent wells, the completion parameters associated with the adjacent wells, the order in which the adjacent wells are brought online, and the order and nature in which subsequent fracking treatments are given, among other factors.

Figure 21:
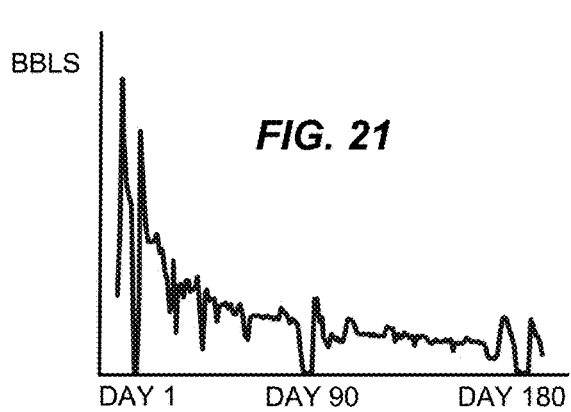
FIG. 21 and FIG. 22 include graph illustrations of well production.
Figure 22:
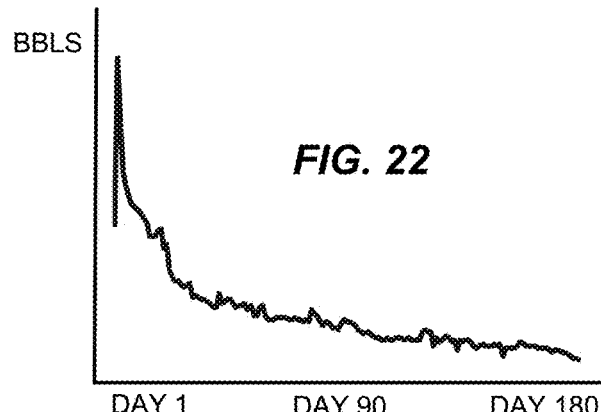

In another example, production and configuration of a well can be influenced by factors other than those specific to a particular well. For example, mechanical failures, maintenance schedules, weather, other logistics influences, or any combination thereof, can influence the production of a well and provide little indication as to the production capabilities of the well. As such, the actual production from a well can be characterized by high variability or periods of no production, as illustrated in FIG. 21. By observing factors that influence production of the well relate to the structure and configuration of the well as opposed to other external factors, the system can establish a production capability, represented for example by a synthetic flow feature variable, as illustrated in FIG. 22.

In particular, it has been found that synthetic variables relating to fracking order, production or flow capability, time and distance synthetic variables relating to proximity of producing wells and other similar synthetic variables correlate more accurately with production and well performance than traditional variables. Accordingly, field models incorporating such synthetic variables, derived from information about the field, provide more accurate projections about well capabilities and performance.

In a particular example, the synthetic variable is derived from a time factor in addition to other factors. For example, a synthetic variable referred to as a proximity depletion variable can be determined based on Euclidean distance between stages of nearby wells, a time difference between completion, and a depletion curve. In another example, a fracking order feature variable can be determined based on fracking end dates of wells proximal to each other and having parallel laterals. In a further example, a synthetic variable can include a fraction hit feature, which quantifies the effect of completing a new infill well in the vicinity of producing wells. In an additional example, a synthetic variable can include a flow feature, which separates the impact of operational policies, such as shut-ins and choke restrictions, to isolate the impact of completion design decisions on production.

Figure 23:
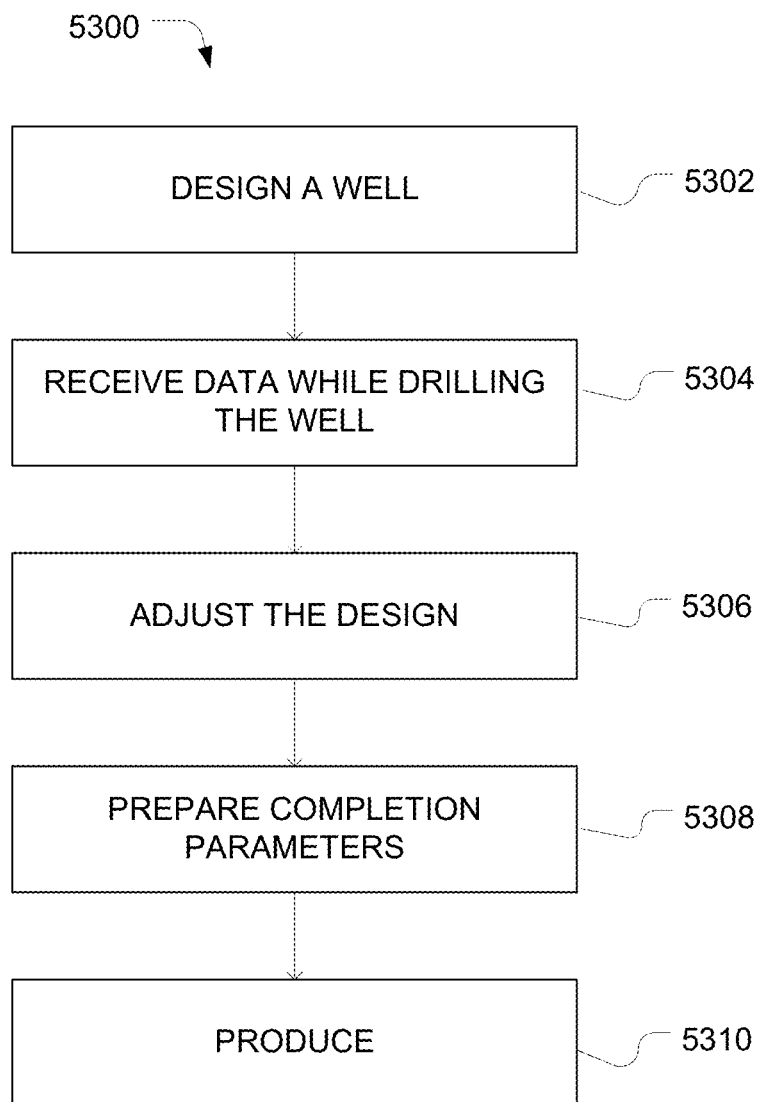
FIG. 23 includes a flow diagram of an exemplary method for production.

In a particular example, as illustrated in FIG. 23, the method 5300 for improving production includes designing a well, as illustrated at 5302. For example, a drilling analysis engine can be used to provide design parameters, such as drilling parameters, for a proposed well. Drilling parameters include location parameters, such as surface location, total vertical depth, azimuth, dip, inclination; configuration parameters, such as number of segments and location; drill parameters, such as depth specific spin rates, weight or pressure on the drill bit, or drill bit type; mud parameters, such as viscosity, mud type, flow rates; the like; or a combination thereof.

As illustrated in 5304, data can be received while drilling the well. Such data can include drilling reports, pressure data, and log data, among other data. In response to the received data, the prescription system, utilizing a drilling analysis engine can adjust the design, as illustrated at 5306.

In addition, the prescription engine can utilize a completion analysis engine to prescribed completion parameters, as illustrated at 5308. Exemplary completion parameters includes treated lateral length, a number of stages, the location of stages or a treated lateral length per stage, clusters (number and spacing), perforation parameters including type, configuration, number, direction, or phasing, and fracking parameters, such as proppant type, proppant amount, fluid type, volume, pressure, rates, duration, or initial or final frac gradients, or a combination thereof.

As illustrated at 5310, the well can produce, and data resulting from such production can be utilized by the system to improve the drilling analysis engine or completion analysis engine and improve prescriptions resulting from the application of the engines.

Figure 24:
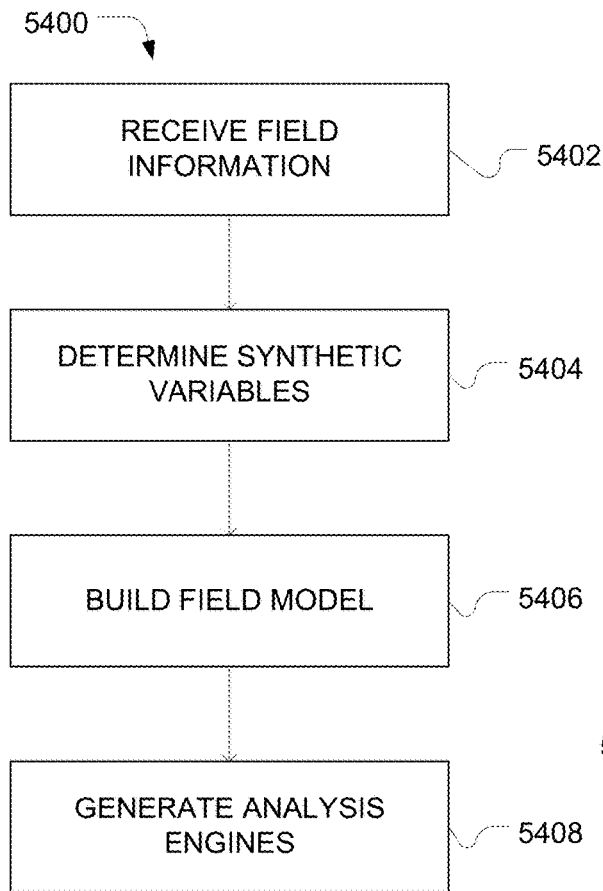
FIG. 24, FIG. 25, and FIG. 26 include flow diagrams of exemplary methods for production.

Such a method can benefit from a field specific model incorporating geological factors, production history and well locations, particularly incorporating synthetic variables. In particular, the field specific model is not a finite element or finite difference model. For example, as illustrated in FIG. 24, a method 5400 includes receiving field information, as illustrated at 5402. The field information can include production data, location of wells, features associated with the geological structure, parameters and configurations used in drilling, completing, and maintaining a given well, as well as depletion curves and other information.

As illustrated at 5404, a set of synthetic variables can be derived from the field information. Such synthetic variables can include a proximity depletion variable, a fracking order feature variable, a fraction hit feature, a flow feature, or a combination thereof.

As illustrated at 5406, the field specific model can be built based on the field information and the synthetic variables. Such a field model can be used by analysis engines to generate prescriptions, such as drilling recipes, completion recipes, postproduction maintenance, treatment, and configuration recipes, as well as predict production from the wells.

Figure 25:
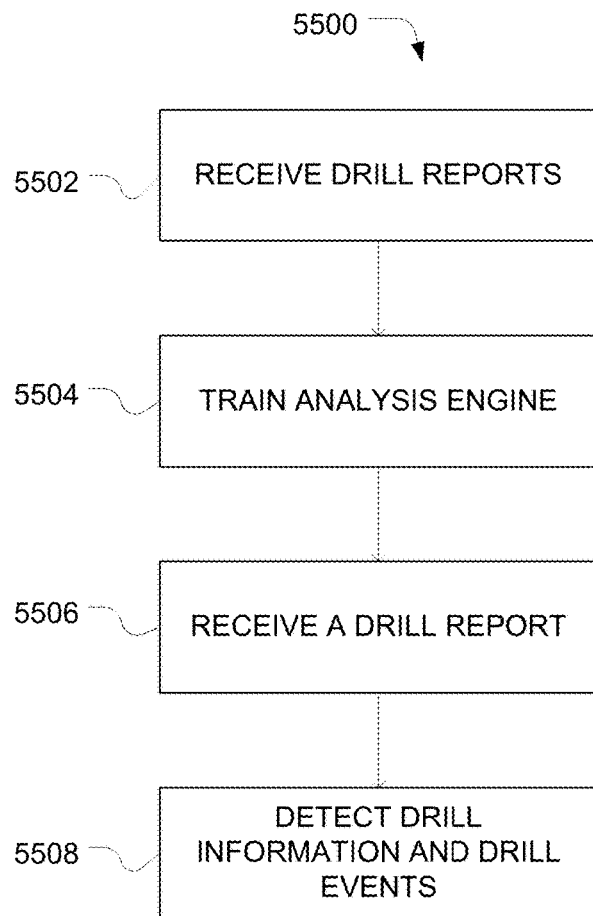

One particular source of field information is the drill reports (unstructured text data). The drill reports include a large number of entries of narrative text with incorporating abbreviations and operator notes having limited syntax and grammar. For a given well, the drill reports can incorporate thousands of entries. The entries in a single drill report can be provided by several operators, each using different abbreviations to address the same factor. In an exemplary method, illustrated in FIG. 25, analyzing such drill reports can be performed automatically. For example, the method 5500 includes receiving historical drill reports, as illustrated at 5502. Based on the historical reports, an analysis engine can be trained, as illustrated at 5504. In particular, the analysis engine can include a neural network or a classification structure.

Once the analysis engine is trained, a new drill report can be received, as illustrated at 5506, and the drill report can be processed using the trained analysis engine to detect drill information and events, as illustrated at 5508. For example, the drill information can include drilling parameters associated with depth, such as spin rates, weight or pressure applied to a drill, mudflow parameters, or other drill information associated depth. Further, drill events such as string events (pulling or inserting the drill string), repair issues (e.g., drill bit damage, pump damage), mud loss, or other events that occurred during drilling can be identified along with an associated depth. The identified drill events are provided as structured data for use in the field specific model. Such drill information and events can be applied to the field specific model for future use in determining drill recipes. Alternatively, such information can be used while drilling a particular well to adjust drill recipes as events occur.

Figure 26:
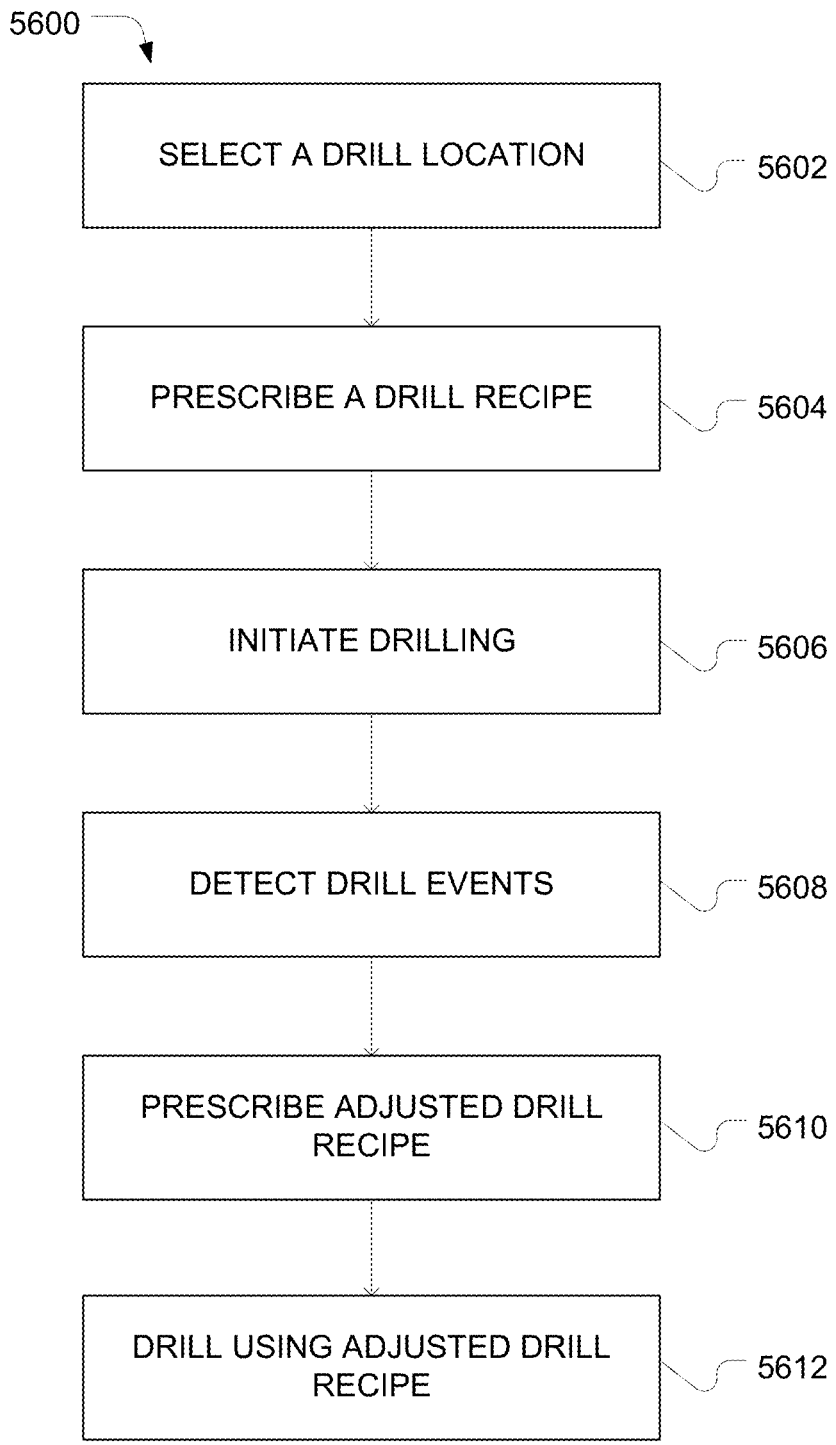

For example, as illustrated in FIG. 26, a method 5600 includes selecting a drill location, as illustrated at 5602. The drill location can include a pad location (e.g., latitude and longitude) and can also include a location within a structure, characterized by total vertical depth (TVD), azimuth, and dip or inclination.

Using a drill analysis engine and the field specific model, a drill recipe can be prescribed, as illustrated at 5604. Exemplary drill recipes include a number of segments, location of such segments, drilling spin rates, weights, mudflow parameters, and other factors relating to the drilling of the well.

As illustrated at 5606, drilling can be initiated in accordance with the drill recipe. For example, drilling can proceed using the established segments and segment locations, as well as spin rates, weights, mudflows, other factors, or a combination thereof.

The system can detect a drill event, as illustrated at 5608. Such events can be detected, for example, by analyzing drill reports. In another example, an operator can directly enter a drill event into the system. Drill events can include deviations or changes in the drilling parameters and can include unexpected events, such as mechanical issues, mud loss, string events, drill bit failure, or other unexpected events.

Based on the detected drill events, the system can prescribe an adjusted drill recipe, as illustrated at 5610. For example, the system can prescribe a drill recipe having a different number of segments or locating segments at different positions to adjust the recipe given the nature of the drill events. In another example, the system can adjust spin rates or weights applied to the drill bit or can adjust mud parameters to suit conditions detected while drilling. As illustrated at 5612, drilling can proceed using the adjusted drill recipe.

Such an approach can be used to limit lost drilling time, the use of resources, such as mud, equipment wear, and ultimately cost associated with drilling a well.

Figure 27:
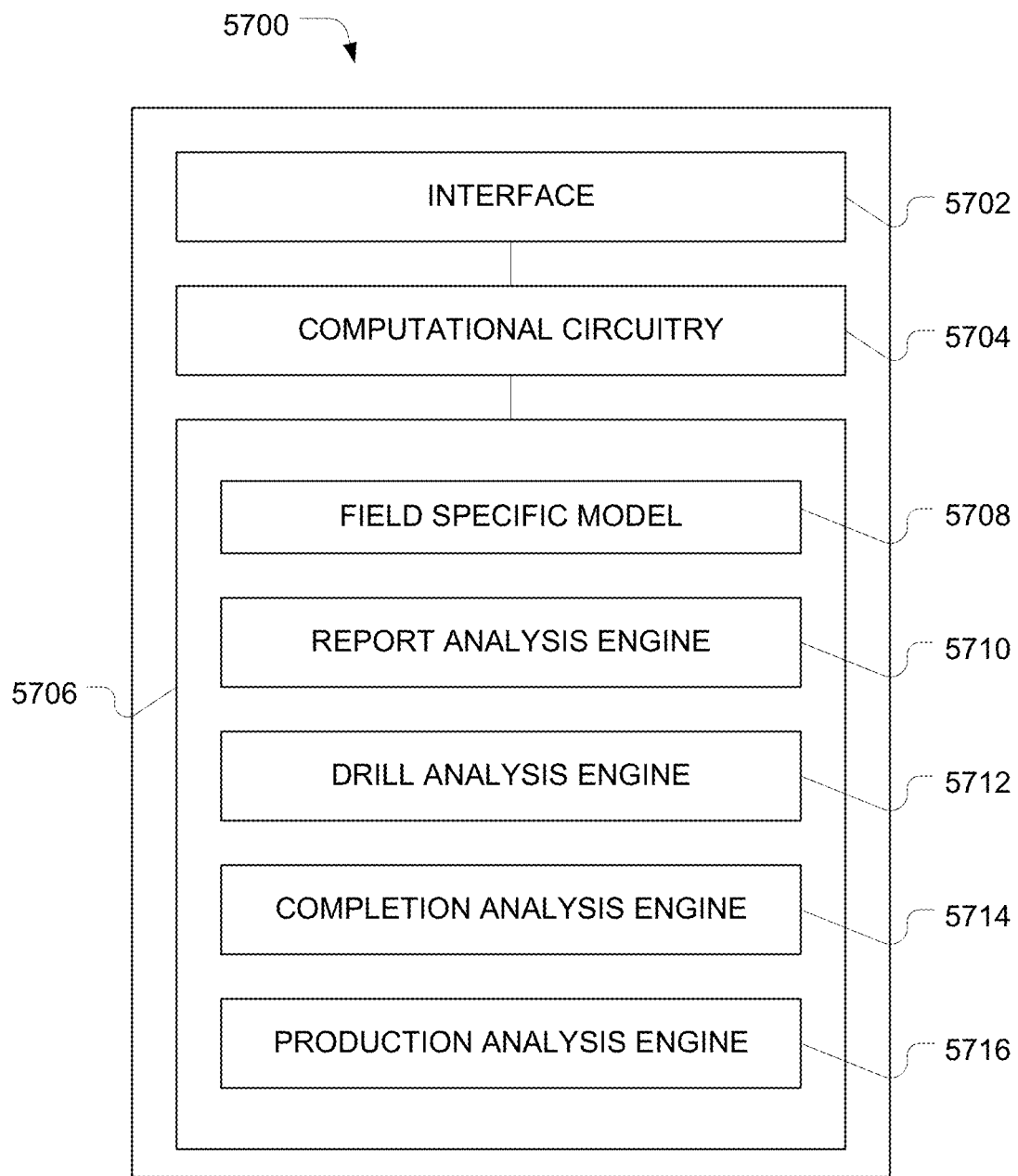
FIG. 27 includes an illustration of an exemplary system.

A system to perform the methods described herein can include a field specific model and engines derived from such a field specific model, such as a report analysis engine, a drilling analysis engine, a completion analysis engine, a production analysis engine, which can each be utilized by a prescription engine to achieve an objective. As illustrated in FIG. 27, the system 5700 can include an interface 5702. The interface 5700 can include network interfaces, equipment interfaces or user interfaces, such as displays, keyboards, and pointer devices. The system 5700 can also interface with other equipment, permitting the system 5700 to adjust parameters on the fly. The system 5700 can also include computational circuitry 5704 configured to implement various procedures and instructions, for example, stored in non-transitory storage 5706. In a particular example, the system can include a field specific model 5708 that incorporates the information associated with a field, including geological information, drilling and production history, synthetic variables, and other factors.

The system can further includes various engines derived from or utilizing the field specific model 5708. Such engines can be implemented as a single unit or can be implemented separately to provide the desired functionality. For example, the system can include a report analysis engine 5710 trained to analyze drill reports, such as historical drill reports or current drill reports. Such a report analysis engine 5710 can provide feedback to further enhance the field specific model 5708 or to provide information useful by other engines in determining parameters and recipes to be used on a given well or throughout a given field. The report analysis engine 5710 can be trained as described above and can incorporated structures, such as a neural network or classification.

In another example, the system 5700 can include a drill analysis engine 5712. In an example, the drill analysis engine 5712 can provide drill recipes associated with a proposed well or can modify a drill recipe as additional information is available, such as through drill events. The drill analysis engine 5712 can be trained as described above and can incorporated structures, such as a neural network or regression.

In an additional example, the system can include a completion analysis engine 5714, which can be used to determine recipes for completing a well. In an example, the completion analysis engine 5714 can be used to determine when additional treatments can be performed on a well, such as additional fracking. The completion analysis engine 5714 can be trained as described above and can incorporated structures, such as a neural network or regression.

In further example, the system 5700 can include a production analysis engine 5716, which can be used to analyze the production, determining a maintenance schedule or maintenance recipe, predict equipment failure, schedule routine maintenance, suggest the installation of artificial lift, suggest implementation of enhanced recovery, and a predicted time or date for maintenance, treatment, lift, or enhanced recovery, as well as other post completion factors associated with producing fluid from a well. The production analysis engine 5716 can be trained as described above and can incorporated structures, such as a neural network, regression, or classification.

Figure 28:
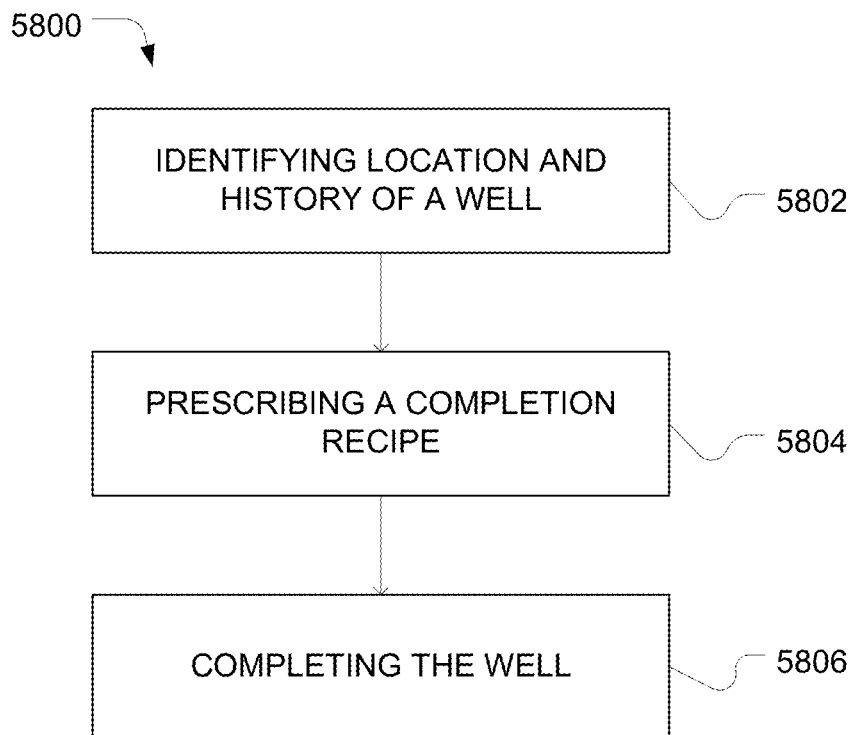
FIG. 28, FIG. 29, FIG. 30, FIG. 31 and FIG. 32 include flow diagrams illustrating exemplary methods for production.

For example, the system can prescribe a completion recipe. As illustrated in FIG. 28, a method 5800 can include identifying a location and history of the well, as illustrated at 5802. The well can be a newly drilled well. Such information can include the drill parameters used in forming the well and other factors such as segmentation and unexpected drilling events. The history can also incorporate information about surrounding wells, and associated production histories and completions.

As illustrated at 5804, the system can prescribe a completion recipe, for example, using a position analysis engine applied to the field specific model. In an example, completion recipe includes a number of stages, perforations parameters, including number, direction, and type, treated lateral length, fracking parameters, such as proppant type, concentration, and amounts, pressure, rates, duration, gradients, and fluid type and volume.

As illustrated 5806, the well can be completed in accordance with the completion recipe.

Figure 29:
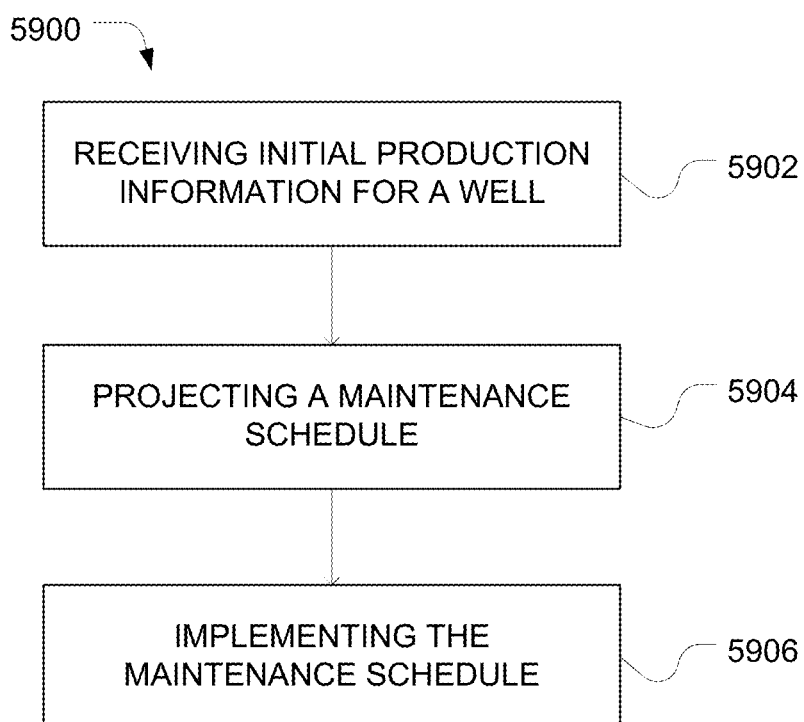

Following completion, cumulative production and maintenance can be associated with a well. As illustrated in FIG. 29, a method 5900 can include receiving initial production information for a well, as illustrated at 5902. For example, the initial production information can include production information for an initial period of time such is 30 days, 60 days, 90 days or 180 days.

Based on such information as well as the field specific model that incorporates production information about other wells within the field, a maintenance schedule can be projected, as illustrated at 5904. The maintenance schedule can incorporate factors such as the desirability to periodically shut-in a well, rework the well, treat the well at a future date, install artificial lift technology at a future date, implement enhanced recovery at a future date, or other factors that influence the cumulative production from the well. Reworking can include drilling additional segments, blocking segments, recompleting, or a combination thereof. A maintenance schedule can also predict failure of equipment associated with the well, such as transfer pumps, sensors, power supplies, or containers.

As illustrated at 5906, the maintenance schedule can be implemented. For example, a well can be treated such as fracking the well at a date proposed by the system. In another example, the well can be shut-in for a period of time or periodically for a given duration as proposed by the system. In another example, the well can be completely reworked, changing the completion parameters based on the proposed reworking provided by the production analysis engine. In a further example, the production analysis engine can predict a date at which an artificial lift mechanism can be installed, as well as a type of lift mechanism to be installed to improve production from the well. Exemplary artificial lift parameters include artificial lift types which includes hydraulic lift, electric submersible pump, gas lift, rod lift, or any combination thereof.

Further, the method 5900 can be applied to the field or applied to a plurality of wells to determine when implementing enhanced recovery at the field or within the plurality of wells is advantageous. Enhanced recovery can include injecting fluids such as water or gas, or injecting surfactants or carbon dioxide to drive production fluids from the reservoir.

Figure 30:
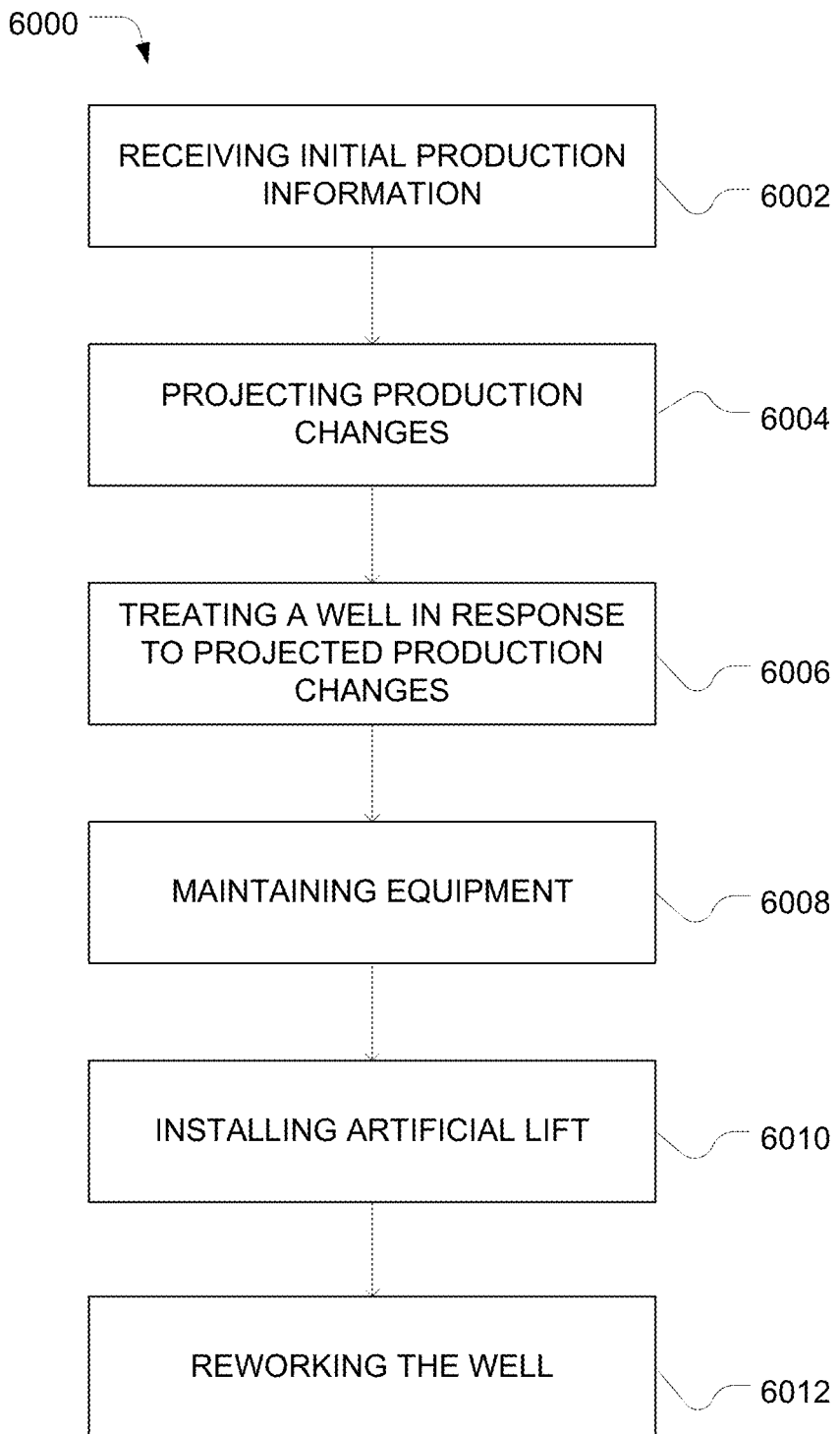

For example, as illustrated in FIG. 30, a method 6000 includes receiving initial production information, as illustrated at 6002. As above, the initial production information can include cumulative production for an initial period, such as 30 days, 60 days, 90 days or 180 days. The production analysis engine can using such information along with the field specific model project production changes, as illustrated at 6004. Such production changes can include a depletion curve or changes in response to reworking, treatments such as fracking, installation of artificial lift, periodic shut-ins, or equipment failures. Production changes can include implementation of enhanced recovery.

Based on projected production changes, the system can prescribe a maintenance schedule that, for example, includes maintaining equipment, installing artificial lift, reworking the well, or periodically treating a well. For example, as illustrated at 6006, the well can be treated in response to the projected production changes. For example, the well can be fracked at a future date proximal to the proposed fracking date to realize improve production from the well. As illustrated at 6008, the equipment associated with the well, such as transfer pumps, containers, sensors, power supplies, or other equipment, can be maintained to prevent equipment failures predicted by the production analysis engine. In a further example, artificial lift can be installed in accordance with a recipe provided by the production analysis engine, as illustrated at 6010. For example the artificial lift recipe can include a proposed date for providing artificial lift, a type of artificial lift, and other parameters associated with the operating of the artificial lift. In a particular example, artificial lift can be installed within a six-month period of the proposed date for installing artificial lift such as within a three-month period.

The system can further project when reworking a well improves production, as illustrated at 6012. For example, the production analysis engine can project a date at which reworking the well improves cumulative production, for example, accessing a completion engine to propose different completion parameters, such as number of stages, perforations, perforation types, fracking parameters, or other completion characteristics. In such a manner, the production analysis engine can project well production from a well, as well as anticipated future costs.

Figure 31:
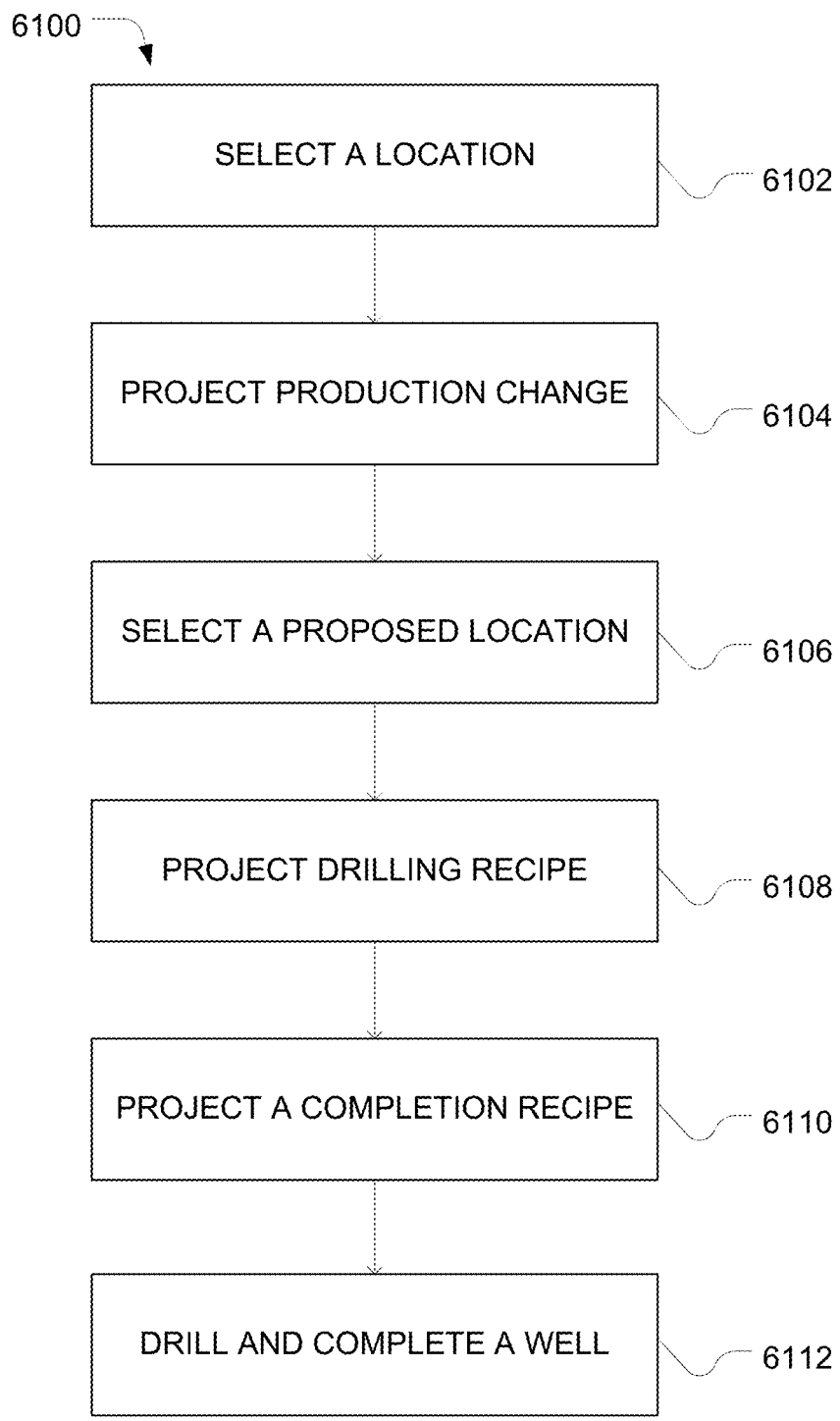

The system can further assist with selecting locations for additional wells. For example, as illustrated in FIG. 31, a method 6100 includes selecting a location, as illustrated at 6102. In an example, in an iterative process, locations can be selected and the production associate with the location can be evaluated to determine whether the location is a desirable location for drilling a well.

As illustrated at 6104, the production changes can be projected based on the proposed location. The proposed location can include a surface location, total vertical depth, azimuth or dip/inclination, or any combination thereof.

Production changes can include the effect of production on adjacent wells, such as a decrease in production from adjacent wells in response to drilling a new well. As illustrated at 6106, the proposed location can be selected, for example, based on a location that provides an improved production from the field. Such improved production can result from the new production derived from the new well minus the loss of production from other adjacent wells.

The system can project a drilling recipe, as illustrated at 6108. The drilling recipe can prescribe parameters and factors, such as a number of segments and segment locations, drilling parameters and mudflow parameters, among others.

The system can also project a completion recipe, as illustrated at 6110. The completion recipe can, for example, include a number of stages, number and type and direction perforations, treatment options, such as fracking parameters, or any combination thereof.

The well can be drilled and completed at the proposed location, as illustrated at 6112, in accordance with the drilling recipe and completion recipe. Optionally, the system can provide feedback and adjust the drilling recipe and completion recipe in response to drilling events or other factors experienced while preparing the well.

Figure 32:
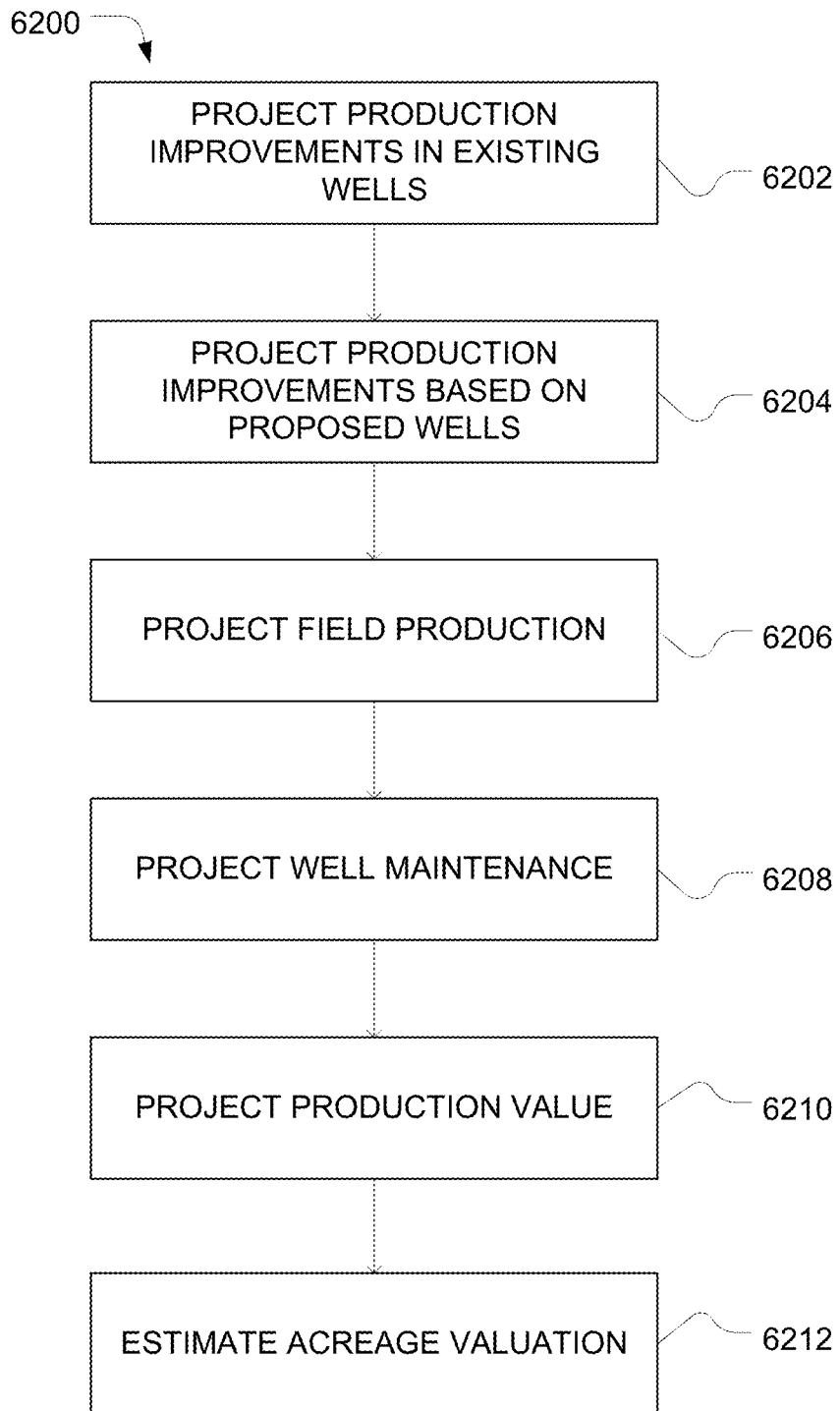

Such methods can lead to improved overall field management, including improved production from the field, as well as reducing costs associated with maintaining the field. For example, as illustrated in FIG. 32, a system 6200 includes projecting production improvements of existing wells, as illustrated at 6202. In an example, existing wells producing with given depletion curves can be influenced by reworking, additional treatments, installation of artificial lift, or other factors. Such methods can also propose enhanced recovery for a field or set of wells.

In addition, the system can project production improvements based on proposed new wells, as illustrated at 6204. For example, as additional wells are added based on projected drill recipes and completion recipes, the wells can provide additional production, while limiting a loss in production from adjacent wells. As such, the system can determine a set of proposed locations and the projected production from drilling wells at the proposed locations or project the effect on total field production based on drilling at the proposed locations. The projected improvements in production from existing wells and improvements based on the drilling proposed new wells can be iteratively performed, leading to the projected field production, as illustrated at 6206. For example, the system can project a field production that results from the implementation of maintenance programs for existing wells in addition to the drilling of new wells.

As above, the system can project well maintenance schedules, as illustrated 6208. Such maintenance schedules can have an influence on both the field production, as well as costs associated with producing from the field. The maintenance schedules can include shut-in schedules, artificial lift installation, equipment types, enhanced recovery or combinations thereof.

Based on the above values, the system can project a production value, as illustrated 6210. Such production value can be used to estimate acreage valuation, as illustrated at 6212. For example, based on available improve production relative to current projected production, the system can estimate a valuation of acreage, which provides an indication to a buyer, seller, or leaser of such acreage regarding whether the proposed pricing of such acreage is high or low. Such factors can be influenced by the future market value of production fluids, such as oil or gas, as well as other economic factors, such as inflation, interest rates, depreciation, and multiples or ratios.

In a first aspect, a method for drilling a well includes prescribing a drill recipe with a drill analysis engine based on a field-specific model, the drill recipe identifying prescribed segments, mud flow parameters, and drill parameters, each prescribed segment of the prescribed segments including a start depth; initiating drilling of the well based on the drill recipe; receiving a drill log in narrative text format; detecting a drill event inconsistent with the drill recipe by analyzing the drill log with a log analysis engine; prescribing an adjusted drill recipe with the drill analysis engine based on the field-specific model in response to the drill event, the adjusted drill recipe including adjusted prescribed segments; and drilling the well based on the adjusted drill recipe.

In an example of the first aspect, the mud flow parameters include depth specific mud flow parameters. For example, the mud flow parameters include mud flow rates. In another example, the mud flow parameters include mud viscosity.

In another example of the first aspect or the above examples, the drill parameters include weight.

In a further example of the first aspect or the above examples, the drill parameters include spin rate.

In an additional example of the first aspect or the above examples, the drill parameters are depth specific drill parameters.

In another example of the first aspect or the above examples, the drill event includes a string event.

In a further example of the first aspect or the above examples, the drill event includes a mud loss event.

In an additional example of the first aspect or the above examples, the drill event includes a depth specific drill rate.

In another example of the first aspect or the above examples, the drill event includes a deviation in drill parameters from the prescribed drill recipe.

In a further example of the first aspect or the above examples, the drill event includes an associated depth.

In an additional example of the first aspect or the above examples, the adjusted drill recipe includes adjusted drill parameters.

In another example of the first aspect or the above examples, the adjusted drill recipe includes adjusted mud flow rates.

In a further example of the first aspect or the above examples, the log analysis engine is a machine learned engine. For example, the machine learned engine includes a neural network model or a classification model.

In an additional example of the first aspect or the above examples, the field specific model includes a synthetic proximity depletion variable. For example, the synthetic proximity depletion variable is derived from Euclidean distance between two wells and associated depletion curves.

In another example of the first aspect or the above examples, prescribing with the drill analysis engine further includes determining a regression model based on a correlation between drill recipe variables, geological variables and objectives using the drill analysis engine and based on the field specific data model.

In a further example of the first aspect or the above examples, prescribing with the drill analysis engine further includes applying a neural network drill analysis engine receiving drill recipe variables, geological variables and objectives based on the field specific data model.

In a second aspect, a method for drilling a well includes prescribing a drill recipe using a drill analysis engine based on a field-specific model, the drill recipe identifying prescribed segments, each prescribed segment of the prescribed segments including a start depth; initiating drilling of the well based on the drill recipe; detecting a drill event inconsistent with the drill recipe; prescribing an adjusted drill recipe using the drill analysis engine based on the field-specific model in response to the drill event, the adjusted drill recipe including adjusted prescribed segments; and drilling the well based on the adjusted drill recipe.

In an example of the second aspect, the method further includes receiving a drill log in narrative text format, wherein detecting includes analyzing the drill log with a log analysis engine. For example, the log analysis engine is a machine learned engine. In an example, the machine learned engine includes a neural network model or a classification model.

In another example of the second aspect or the above examples, the drill recipe further includes mud flow parameters and drill parameters. For example, the mud flow parameters include depth specific mud flow parameters. In an example, the mud flow parameters include mud flow rates. In a further example, the mud flow parameters include mud viscosity. In an additional example, the drill parameters include weight. In another example, the drill parameters include spin rate. In a further example, the drill parameters are depth specific drill parameters.

In a further example of the second aspect or the above examples, the drill event includes a string event.

In an additional example of the second aspect or the above examples, the drill event includes a mud loss event.

In another example of the second aspect or the above examples, the drill event includes a deviation in drill parameters from the prescribed drill recipe.

In a further example of the second aspect or the above examples, the drill event includes an associated depth.

In an additional example of the second aspect or the above examples, the adjusted drill recipe includes adjusted depth specific drill parameters.

In another example of the second aspect or the above examples, the adjusted drill recipe includes adjusted mud flow rates.

In a further example of the second aspect or the above examples, prescribing includes prescribing using a neural network or a regression based on a correlation determined from the field specific model.

In an additional example of the second aspect or the above examples, the field specific model includes a synthetic proximity depletion variable.

In another example of the second aspect or the above examples, the synthetic proximity depletion variable is derived from Euclidean distance between two wells and associated depletion curves.

In a third aspect, a system includes a field-specific model; a log analysis engine; a drill analysis engine; an interface; and computational circuitry in communication with the field-specific model, the log analysis engine, the drill analysis engine, and the interface. The computational circuitry to prescribe a drill recipe using the drill analysis engine based on the field-specific model, the drill recipe identifying prescribed segments, mud flow parameters, and drill parameters, each prescribed segment of the prescribed segments including an associated depth; receive a drill log in narrative text format via the interface; detect a drill event inconsistent with the drill recipe by analyzing the drill log with the log analysis engine; and prescribe an adjusted drill recipe using the drill analysis engine based on the field-specific model in response to the drill event, the adjusted drill recipe including adjusted prescribed segments.

In an example of the third aspect, the mud flow parameters include depth specific mud flow parameters. For example, the mud flow parameters include mud flow rates.

In another example of the third aspect and the above examples, the drill parameters include weight.

In a further example of the third aspect and the above examples, the drill parameters include spin rate.

In an additional example of the third aspect and the above examples, the drill parameters are depth specific drill parameters.

In another example of the third aspect and the above examples, the drill event includes a string event.

In a further example of the third aspect and the above examples, the drill event includes a mud loss event.

In an additional example of the third aspect and the above examples, the drill event includes a drill rate.

In another example of the third aspect and the above examples, the drill event includes a deviation in drill parameters from the prescribed drill recipe.

In a further example of the third aspect and the above examples, the drill event includes an associated depth.

In an additional example of the third aspect and the above examples, the adjusted drill recipe includes adjusted drill parameters.

In another example of the third aspect and the above examples, the adjusted drill recipe includes adjusted mud flow rates.

In a further example of the third aspect and the above examples, the log analysis engine is a machine learned engine. For example, the machine learned engine includes a neural network model or a classification model.

In an additional example of the third aspect and the above examples, the field specific model includes a synthetic proximity depletion variable. For example, the synthetic distance/time variable is derived from Euclidean distance between two wells and associated depletion curves.

In another example of the third aspect and the above examples, prescribing with the drill analysis engine further includes determining a correlation between drill recipe variables, geological variables and objectives using the drill analysis engine and based on the field specific data model.

In a further example of the third aspect and the above examples, prescribing with the drill analysis engine further includes applying a neural network drill analysis engine receiving drill recipe variables, geological variables and objectives based on the field specific data model.

In an additional example of the third aspect and the above examples, the method further includes a drilling rig configured to drill a well in accordance with the drill recipe.

In a fourth aspect, a method for determining a drill event includes receiving a set of historic drill reports with annotations, the historic drill reports including a plurality of entries including multiple acronyms relating to a single drilling factor, a set of entries of the plurality of entries indicating an associated depth; training a report analysis engine utilizing the historic drill reports and annotations; receiving a drill report associated with a well; and determining a drill event and associated depth utilizing the report analysis engine applied to the drill report.

In an example of the fourth aspect, the drill event includes a mud loss event.

In another example of the fourth aspect and the above examples, the drill event includes a string event.

In a further example of the fourth aspect and the above examples, the drill event includes a depth specific drill rate.

In an additional example of the fourth aspect and the above examples, the drill event includes a deviation in drill parameters from the prescribed drill recipe.

In another example of the fourth aspect and the above examples, the drill event includes an associated depth.

In a further example of the fourth aspect and the above examples, the report analysis engine includes a neural network.

In an additional example of the fourth aspect and the above examples, the report analysis engine includes a classification model.

In another example of the fourth aspect and the above examples, the historic drill reports are unstructured data in the form of text.

In an additional example of the fourth aspect and the above examples, the method further includes incorporating the drill event into a field specific model.

In another example of the fourth aspect and the above examples, the method further includes determining an adjusted drilling parameters based on the drill event using a drilling analysis engine.

In a fifth aspect, a method for determining a drill event includes receiving a set of historic drill reports with annotations, the historic drill reports being unstructured data in the form of text, the historic drill reports including a plurality of entries including multiple acronyms relating to a single drilling factor, a set of entries of the plurality of entries indicating an associated depth; training a report analysis engine utilizing the historic drill reports and annotations; receiving a drill report associated with a well; determining a drill event and associated depth utilizing the report analysis engine applied to the drill report; and determining an adjusted drilling parameters based on the drill event using a drilling analysis engine.

In an example of the fifth aspect, the drill event includes a mud loss event.

In another example of the fifth aspect and the above examples, the drill event includes a string event.

In an additional example of the fifth aspect and the above examples, the drill event includes a depth specific drill rate.

In another example of the fifth aspect and the above examples, the drill event includes a deviation in drill parameters from the prescribed drill recipe.

In a further example of the fifth aspect and the above examples, the drill event includes an associated depth.

In an additional example of the fifth aspect and the above examples, the report analysis engine includes a neural network.

In another example of the fifth aspect and the above examples, the report analysis engine includes a classification model.

In an additional example of the fifth aspect and the above examples, the method further includes incorporating the drill event into a field specific model.

In a sixth aspect, a method of drilling a well includes receiving depth specific drill parameters associated with drilling wells within a field; receiving drilling report entries associated with drilling the wells within the field; applying a report analysis engine to the drilling report entries to determine a drilling event; determining a field-specific drilling model utilizing the depth specific drill parameters and drilling event; and prescribing a drilling recipe using a drilling analysis engine applied to the field-specific drilling model; and drilling the well in accordance with the drilling recipe.

In an example of the sixth aspect, the method further includes receiving geological parameters associated with the field, wherein determining the field-specific drilling model utilizes the geological parameters.

In another example of the sixth aspect and the above examples, the drilling recipe includes a number of segments and associated depths.

In a further example of the sixth aspect and the above examples, the drilling recipe includes depth-specific drilling parameters. For example, the depth-specific drilling parameters include spin rate and weight.

In an additional example of the sixth aspect and the above examples, the method further includes receiving mud flow parameters, wherein determining the field-specific drilling model includes determining the field-specific drilling model utilizing the mud flow parameters. For example, the mud flow parameters include depth-specific mud flow rates and viscosity.

In another example of the sixth aspect and the above examples, the drilling event includes associated depth.

In a further example of the sixth aspect and the above examples, the drilling event includes a mud loss event.

In an additional example of the sixth aspect and the above examples, the drilling event includes a drill bit event.

In a seventh aspect, a method for drilling a well includes receiving drilling report entries associated with drilling the wells within a field; applying a report analysis engine to the drilling report entries to determine a drilling event and depth-specific drilling parameters; determining a field-specific drilling model utilizing the depth-specific drill parameters and the drilling event; prescribing a drilling recipe using a drilling analysis engine applied to the field-specific drilling model; and drilling the well in accordance with the drilling recipe.

In an example of the seventh aspect, the method further includes receiving geological parameters associated with the field, wherein determining the field-specific drilling model utilizes the geological parameters.

In another example of the seventh aspect and the above examples, the drilling recipe includes a number of segments and associated depths.

In a further example of the seventh aspect and the above examples, the drilling recipe includes depth-specific drilling parameters. For example, the depth-specific drilling parameters include spin rate and weight.

In an additional example of the seventh aspect and the above examples, the method further includes receiving mud flow parameters, wherein determining the field-specific drilling model includes determining the field-specific drilling model utilizing the mud flow parameters. For example, the mud flow parameters include depth-specific mud flow rates and viscosity.

In a further example of the seventh aspect and the above examples, the drilling event includes associated depth.

In an additional example of the seventh aspect and the above examples, the drilling event includes a mud loss event.

In another example of the seventh aspect and the above examples, the drilling event includes a drill bit event.

In an eighth aspect, a method for completing a well includes receiving completion parameters associated with wells within a field, the completion parameters including casing parameters, perforation parameters, and fracking parameters; determining a field-specific model utilizing the completion parameters; and prescribing a completion recipe using a completion analysis engine applied to the field-specific model, the completion recipe including prescribed perforation parameters and prescribed fracking parameters, the completion analysis engine including a neural network derived from the field-specific model or a correlation of features in the field-specific model; and completing the well in accordance with the completion recipe including performing perforation in accordance with the perforation parameters and fracking in accordance with the fracking parameters.

In an example of the eighth aspect, the method further includes receiving geological parameters associated with the field, wherein determining the field-specific model utilizes the geological parameters.

In another example of the eighth aspect and the above examples, the perforation parameters include location, number of perforations, or any combination thereof.

In a further example of the eighth aspect and the above examples, the fracking parameters include pressure, proppant composition, proppant amount, flow rates, or a combination thereof.

In an additional example of the eighth aspect and the above examples, the field-specific model incorporates a proximity depletion synthetic variable derived from the distance to adjacent wells from the well and the time of production of the adjacent wells.

In a ninth aspect, a method for completing a well includes receiving completion parameters associated with wells within a field; determining a field-specific model utilizing the completion parameters; and prescribing a completion recipe for the using a location of the well and a completion analysis engine applied to the field-specific model; and completing the well in accordance with the completion recipe.

In an example of the ninth aspect, the method further includes receiving geological parameters associated with the field, wherein determining the field-specific model utilizes the geological parameters.

In another example of the ninth aspect and the above examples, the completion recipe includes casing parameters. For example, the casing parameters include cement parameters.

In a further example of the ninth aspect and the above examples, the completion recipe includes perforation parameters. For example, the perforation parameters include location. In another example, the perforation parameters include number of perforations.

In an additional example of the ninth aspect and the above examples, the completion recipe includes fracking parameters. For example, the fracking parameters include pressure. In another example, the fracking parameters include proppant amount. In an additional example, the fracking parameters include proppant composition. In a further example, the fracking parameters include flow rate.

In another example of the ninth aspect and the above examples, the field-specific model incorporates a proximity depletion synthetic variable derived from the distance to adjacent wells from the well and the time of production of the adjacent wells.

In a further example of the ninth aspect and the above examples, the completion analysis engine includes a neural network.

In an additional example of the ninth aspect and the above examples, the completion analysis engine includes a regression based on a correlation associating features of the field-specific model.

In a tenth aspect, a method for completing a well includes receiving completion parameters associated with a well within a field; projecting a production of the well based on the completion parameters using a completion engine applied to a field-specific model; prescribing proposed completion parameters for the well to comply with a production objective using the completion engine applied to the field-specific model; projecting a proposed production based on the proposed completion parameters using the completion engine applied to the field-specific model; and recompleting the well in accordance with the proposed completion parameters.

In an example of the tenth aspect, the method further includes receiving a location of the well, wherein projecting and prescribing are based on the location. For example, the location includes a horizontal location within the geological structure.

In another example of the tenth aspect and the above examples, the method further includes receiving geological parameters associated with the field, wherein projecting and prescribing are based on the geological parameters.

In a further example of the tenth aspect and the above examples, the completion parameters include casing parameters.

In an additional example of the tenth aspect and the above examples, the completion parameters include identification of stages.

In another example of the tenth aspect and the above examples, the completion parameters include perforation parameters. For example, the perforation parameters include location. In another example, the perforation parameters include number of perforations.

In a further example of the tenth aspect and the above examples, the completion parameters include fracking parameters. For example, the fracking parameters include pressure. In another example, the fracking parameters include proppant amount. In a further example, the fracking parameters include proppant composition. In an additional example, the fracking parameters include flow rate.

In an additional example of the tenth aspect and the above examples, the field-specific model incorporates a proximity depletion synthetic variable derived from the distance to adjacent wells from the well and the time of production of the adjacent wells.

In another example of the tenth aspect and the above examples, the completion engine includes a neural network.

In a further example of the tenth aspect and the above examples, the completion analysis engine includes a regression based on a correlation associating features of the field-specific model.

In an additional example of the tenth aspect and the above examples, projecting production include projecting cumulative production.

In another example of the tenth aspect and the above examples, the method further includes projecting a production of an adjacent well proximal to the well.

In a further example of the tenth aspect and the above examples, the method further includes comparing a recompletion cost to benefits associated with the proposed production.

In an eleventh aspect, a method for maintaining a well includes receiving production information associated with wells within a field; deriving a field specific model from the production information; receiving initial production information associated with the well; projecting a maintenance schedule associated with the well using a production analysis engine applied to the field specific model, the maintenance schedule including a maintenance event and an associated date; and implementing the maintenance schedule on the well.

In an example of the eleventh aspect, the maintenance event includes fracking. For example, the projected maintenance schedule includes fracking parameters. In an example, the fracking parameters include pressure. In another example, the fracking parameters include proppant amount. In an additional example, the fracking parameters include proppant composition. In a further example, the fracking parameters include flow rate.

In another example of the eleventh aspect and the above examples, the maintenance event includes reworking. For example, the projected maintenance schedule includes projected completion parameters for use during reworking.

In a further example of the eleventh aspect and the above examples, the maintenance schedule includes shut-in parameters. For example, the projected maintenance schedule includes a time and a duration of a shut-in.

In an additional example of the eleventh aspect and the above examples, the production analysis engine includes a neural network derived from the field specific model.

In another example of the eleventh aspect and the above examples, the production analysis engine include a regression based on a correlation associating features of the field-specific model.

In a twelfth aspect, a method for maintaining a well includes receiving production information associated with wells within a field; deriving a field specific model from the production information; receiving production information associated with the well; projecting production changes associated with fracking the well at a projected date, the projecting using a production analysis engine applied to the field specific model, the projecting including determining a set of fracking parameters; and fracking the well in accordance with the fracking parameters.

In an example of the twelfth aspect, the fracking parameters include pressure.

In another example of the twelfth aspect and the above examples, the fracking parameters include proppant amount.

In a further example of the twelfth aspect and the above examples, the fracking parameters include proppant composition.

In an additional example of the twelfth aspect and the above examples, the fracking parameters include flow rate.

In another example of the twelfth aspect and the above examples, the production analysis engine includes a neural network derived from the field specific model.

In a further example of the twelfth aspect and the above examples, the production analysis engine include a correlation associating features of the field-specific model.

In a thirteenth aspect, a method for producing a well includes receiving production information associated with wells within a field; deriving a field specific model from the production information; receiving production information associated with the well; projecting production changes associated with installing artificial lift at the well at a projected date, the projecting using a production analysis engine applied to the field specific model, the projecting including determining a set of artificial lift parameters; and installing the artificial lift at the well in accordance with the artificial lift parameters.

In an example of the thirteenth aspect, the artificial lift parameters include an artificial lift type. For example, the artificial lift type includes a hydraulic pumping system. In another example, the artificial lift type includes an electric submersible pump. In an additional example, the artificial lift type includes a gas lift system. In another example, the artificial lift type includes a rod lift system.

In another example of the thirteenth aspect and the above examples, installing includes installing within 6 months of the projected date. For example, installing includes installing within 3 months of the projected date.

In a further example of the thirteenth aspect and the above examples, the production analysis engine includes a neural network, a regression, or a classification derived from the field specific model.

In an additional example of the thirteenth aspect and the above examples, the production analysis engine include a correlation associating features of the field-specific model.

In another example of the thirteenth aspect and the above examples, the method further includes projecting a difference in revenue.

In a fourteenth aspect, a method for maintaining equipment associated with a well includes receiving production and maintenance information associated with wells within a field; deriving a field specific model from the production and maintenance information; receiving production information and equipment information associated with the well; projecting a maintenance event associated with the equipment associated with the well and an associated projected date, the projecting using a production analysis engine applied to the field specific model; and performing preventative maintenance on the equipment associated with the well prior to the associated projected date.

In an example of the fourteenth aspect, the maintenance event includes a failure of artificial lift equipment.

In another example of the fourteenth aspect and the above examples, the maintenance event includes a failure of a transfer pump.

In a further example of the fourteenth aspect and the above examples, the maintenance event includes a failure of a sensor.

In an additional example of the fourteenth aspect and the above examples, the maintenance event includes a failure of a holding tank.

In another example of the fourteenth aspect and the above examples, the production analysis engine includes a neural network derived from the field specific model.

In a further example of the fourteenth aspect and the above examples, the production analysis engine includes a regression based on a correlation associating features of the field-specific model.

In an additional example of the fourteenth aspect and the above examples, the method further includes projecting a difference in revenue.

In another example of the fourteenth aspect and the above examples, the method further includes projecting field maintenance costs.

In a fifteenth aspect, a method of producing fluids from a geological structure includes receiving field information associated with producing wells of a field; deriving a field specific model based on the field information, the field specific model including a proximity depletion synthetic variable and a fraction hit synthetic variable; identifying a proposed location based on the application of field management engine to the field specific model, the field management engine projecting a decrease in production from wells proximal to the location and projecting an improvement in a production objective; and drilling a well at the proposed location.

In an example of the fifteenth aspect, the field information includes production values and well locations.

In another example of the fifteenth aspect and the above examples, the well location includes horizontal placement.

In a further example of the fifteenth aspect and the above examples, the field information includes geological information.

In an additional example of the fifteenth aspect and the above examples, the field specific model further includes a fracking order synthetic variable.

In another example of the fifteenth aspect and the above examples, the field management engine includes a neural network derived from the field specific model.

In a further example of the fifteenth aspect and the above examples, the field management engine includes a regression based on correlation between the proximity depletion synthetic variable, the fraction hit synthetic variable, and production values.

In an additional example of the fifteenth aspect and the above examples, the method further includes projecting a production of the well. For example, the production is cumulative production.

In another example of the fifteenth aspect and the above examples, the method further includes projecting a production of a plurality of wells associated with the field.

In a sixteenth aspect, a method of producing fluids from a geological structure includes iteratively identifying a location in a field; projecting a decrease in production from wells proximal to the location and a change in a production objective, the projecting based on application of a field management engine to a field specific model, the field specific model including a proximity depletion synthetic variable and a fraction hit synthetic variable; selecting a proposed location based on projecting an improvement in the production objective; and drilling a well at the proposed location.

In an example of the sixteenth aspect, the method further includes receiving field information associated with producing wells of the field; and deriving the field specific model based on the field information.

In another example of the sixteenth aspect and the above examples, the field information includes production values and well locations. For example, the well location includes horizontal placement.

In a further example of the sixteenth aspect and the above examples, the field information includes geological information.

In an additional example of the sixteenth aspect and the above examples, the field specific model further includes a fracking order synthetic variable.

In another example of the sixteenth aspect and the above examples, the field management engine includes a neural network derived from the field specific model.

In a further example of the sixteenth aspect and the above examples, the field management engine includes a regression based on correlation between the proximity depletion synthetic variable, the fraction hit synthetic variable, and production values.

In an additional example of the sixteenth aspect and the above examples, the method further includes projecting a production of the well. For example, the production is cumulative production.

In a seventeenth aspect, a method of managing production in a field includes projecting a first production improvement associated with maintenance of existing wells with a production analysis engine applied to a field specific model; projecting a second production improvement associated with drilling new wells; projecting a field maintenance schedule with the production analysis engine applied to a field specific model; determining a production value associated with the field.

In an example of the seventeenth aspect, projecting the second production improvement includes projecting a production decrease associated with a well proximal to a new well.

In another example of the seventeenth aspect and the above examples, projecting the first production improvement includes projecting a well rework.

In a further example of the seventeenth aspect and the above examples, projecting the first production improvement includes projecting a recompleting a well.

In an additional example of the seventeenth aspect and the above examples, projecting the first production improvement includes projecting production following installation of artificial lift.

In another example of the seventeenth aspect and the above examples, projecting the first production improvement includes projecting a shut-in schedule for a well.

In a further example of the seventeenth aspect and the above examples, projecting the second production improvements includes identifying a location of a new well.

In an additional example of the seventeenth aspect and the above examples, projecting the second production improvements includes projecting a drilling recipe of the new well at the location. For example, the drilling recipe includes a number of stages and associated depths. In an example, the drilling recipe includes drilling parameters or mud parameters. In another example, projecting the drilling recipe includes projecting with a drill analysis engine. For example, the drill analysis engine includes a neural network derived from the field specific model. In a further example, the drill analysis engine includes a regression based on a correlation derived from the field specific model.

In another example of the seventeenth aspect and the above examples, projecting the second production improvements includes projecting a completion recipe of the new well at the location. For example, projecting the completion recipe includes projecting with a completion analysis engine. In an example, the completion analysis engine includes a neural network derived from the field specific model. In another example, the completion analysis engine includes a regression based on a correlation derived from the field specific model.

In a further example of the seventeenth aspect and the above examples, projecting the second production improvements include projecting using the production analysis engine applied to the field specific model.

In an additional example of the seventeenth aspect and the above examples, the production analysis engine includes a neural network model.

In another example of the seventeenth aspect and the above examples, the production analysis engine includes a regression of a correlation derived from the field specific model.

In an eighteenth aspect, a method of analyzing an offered well includes receiving production information and a location associated with an offered well in a field; projecting a depletion curve based on the production information; projecting an improved production in response to maintenance of the offered well using a production engine derived from a field-specific model; determining a value difference based on the improved production relative to the depletion curve.

In an example of the eighteenth aspect, the production engine includes a neural network derived from the field-specific model.

In another example of the eighteenth aspect and the above examples, the production engine includes a regression based on a correlation derived from the field-specific model.

In a further example of the eighteenth aspect and the above examples, the maintenance includes fracking. For example, projecting the improved production includes projecting refracking parameters. In an example, the refracking parameters include pressure. In another example, the refracking parameters include proppant amount. In a further example, the refracking parameters include proppant composition. In an additional example, the refracking parameters include flow rate.

In an additional example of the eighteenth aspect and the above examples, the maintenance includes reworking. For example, projecting the improved production includes projecting completion parameters for use during reworking.

In another example of the eighteenth aspect and the above examples, the maintenance includes well shut-ins. For example, projecting the improved production includes projecting a time and a duration of a shut-in.

In an additional example of the eighteenth aspect and the above examples, the maintenance includes installing artificial lift. For example, projecting the improved production includes projecting an artificial lift type. In an example, the artificial lift type includes a hydraulic pumping system. In another example, the artificial lift type includes an electric submersible pump. In an additional example, the artificial lift type includes a gas lift system. In a further example, the artificial lift type includes a rod lift system.

In another example of the eighteenth aspect and the above examples, the maintenance includes implementing enhanced recovery.

Note that not all of the activities described above in the general description or the examples are required, that a portion of a specific activity may not be required, and that one or more further activities may be performed in addition to those described. Still further, the orders in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method for completing a well, the method comprising:
   receiving completion parameters associated with wells within a field, the field having field characteristics including geological, geophysical, petrophysical, lithological, and mineralogical characteristics, the completion parameters including casing parameters, perforation parameters, and fracking parameters, a first portion of the completion parameters being received in a form of structured data, and a second portion of the completion parameters being received in a form of unstructured data;
   transforming the unstructured data into transformed structured data;
   deriving one or more synthetic variables from the received completion parameters in the form of the structured data and the transformed structured data, wherein the one or more synthetic variables comprise a proximity depletion synthetic variable derived from, at least, distances between and among adjacent wells, and associated depletion curves;
   based on the one or more synthetic variables and further based on the received completion parameters in the form of the structured data and the transformed structured data, building a plurality of field-specific models, each of the plurality of field-specific models being specific to the field characteristics of the field;
   receiving data associated with a new well associated with the field;
   selecting one of the plurality of field-specific models;
   based on the received data associated with the new well and the selected field-specific model, prescribing a completion recipe using a completion analysis engine, the completion recipe including prescribed perforation parameters and prescribed fracking parameters; and
   completing the new well in accordance with the completion recipe including performing perforation in accordance with the prescribed perforation parameters and fracking in accordance with the prescribed fracking parameters.

2. The method of claim 1, wherein the perforation parameters include location, number of perforations, or any combination thereof.

3. The method of claim 1, wherein the fracking parameters include pressure, proppant composition, proppant amount, flow rates, or a combination thereof.

4. A method for completing a well, the method comprising:
- receiving completion parameters associated with wells within a field, the field having field characteristics including geological, geophysical, petrophysical, lithological, and mineralogical characteristics, a first portion of the completion parameters being received in a form of structured data, and a second portion of the completion parameters being received in a form of unstructured data;
- transforming the unstructured data into transformed structured data;
- deriving one or more synthetic variables from the received completion parameters in the form of the structured data and the transformed structured data, wherein the one or more synthetic variables comprise a proximity depletion synthetic variable derived from, at least, distances between and among adjacent wells, and associated depletion curves;
- based on the one or more synthetic variables and further based on the received completion parameters in the form of the structured data and the transformed structured data, building a plurality of field-specific models, each of the plurality of field-specific models being specific to the field characteristics of the field;
- receiving data associated with a new well associated with the field;
- selecting one of the plurality of field-specific models;
- based on the received data associated with the new well and the selected field-specific model, prescribing a completion recipe using a completion analysis engine;
- begin completing the new well in accordance with the completion recipe;
- receiving additional completion data associated with the new well;
- based on the received additional completion data associated with the new well and the selected field-specific model, prescribing an updated completion recipe; and
- continue completing the new well in accordance with the updated completion recipe.

5. The method of claim 4, wherein the completion recipe and the updated completion recipe include casing parameters.

6. The method of claim 5, wherein the casing parameters include cement parameters.

7. The method of claim 4, wherein the completion recipe and the updated completion recipe include perforation parameters.

8. The method of claim 7, wherein the perforation parameters include location.

9. The method of claim 7, wherein the perforation parameters include number of perforations.

10. The method of claim 4, wherein the completion recipe and the updated completion recipe include fracking parameters.

11. The method of claim 10, wherein the fracking parameters include pressure.

12. The method of claim 10, wherein the fracking parameters include proppant amount.

13. The method of claim 10, wherein the fracking parameters include proppant composition.

14. The method of claim 10, wherein the fracking parameters include flow rate.

15. The method of claim 4, wherein each of the plurality of field-specific models includes a neural network, a regression model, or a combination thereof.

16. The method of claim 4, wherein selecting the one of the plurality of field-specific models comprises:
- determining a test set and validating each of the plurality of field-specific models using the test set; and
- based on results of the validation, selecting the one of the plurality of field-specific models.

17. The method of claim 4, wherein the unstructured data comprises one or more videos and/or one or more sound files.

18. The method of claim 4, wherein the unstructured data comprises one or more text files and/or one or more image files.

19. The method of claim 1, wherein the data associated with the new well comprises actual data or simulated data.

20. The method of claim 4, wherein the data associated with the new well comprises actual data or simulated data.

* * * * *